United States Patent
Henry et al.

(10) Patent No.: US 11,541,163 B2
(45) Date of Patent: Jan. 3, 2023

(54) HOLLOW ORGAN IRRIGATION SYSTEMS

(71) Applicant: Hollister Incorporated, Libertyville, IL (US)

(72) Inventors: Jerome A. Henry, Castlebar (IE); William K. Arnold, Gurnee, IL (US); Donald V. Matesi, Wauconda, IL (US); Denise Gamblin, Leeds (GB); Jeanne E. Lee, Libertyville, IL (US); Peng Lin, Buffalo Grove, IL (US); Malford E. Cullum, Grayslake, IL (US)

(73) Assignee: Hollister Incorporated, Libertyville, IL (US)

( * ) Notice: Subject to any disclaimer, the term of this patent is extended or adjusted under 35 U.S.C. 154(b) by 55 days.

(21) Appl. No.: 16/633,954

(22) PCT Filed: Aug. 23, 2018

(86) PCT No.: PCT/US2018/047659
§ 371 (c)(1),
(2) Date: Jan. 24, 2020

(87) PCT Pub. No.: WO2019/040694
PCT Pub. Date: Feb. 28, 2019

(65) Prior Publication Data
US 2020/0206411 A1 Jul. 2, 2020

Related U.S. Application Data

(60) Provisional application No. 62/549,713, filed on Aug. 24, 2017.

(51) Int. Cl.
*A61M 3/02* (2006.01)

(52) U.S. Cl.
CPC ........ *A61M 3/0262* (2013.01); *A61M 3/0266* (2013.01); *A61M 3/0295* (2013.01); *A61M 2210/1067* (2013.01)

(58) Field of Classification Search
CPC .... A61M 3/02; A61M 3/0233; A61M 3/0237; A61M 3/0241; A61M 3/0245;
(Continued)

(56) References Cited

U.S. PATENT DOCUMENTS 3,754,553 A * 8/1973 Hewitt ................ A61M 3/0262
604/204
4,324,242 A * 4/1982 Cross .................. A61M 3/0262
604/911
(Continued)

FOREIGN PATENT DOCUMENTS

WO WO-2015031851 A2 * 3/2015 .......... A61M 3/0262
WO WO 2016/007536 A1 1/2016
(Continued)

OTHER PUBLICATIONS

International Search Report and Written Opinion of the ISA for PCT/US2018/047659 dated Feb. 11, 2019.

*Primary Examiner* — Bradley J Osinski
(74) *Attorney, Agent, or Firm* — Cook Alex Ltd.

(57) ABSTRACT

Components for use in hollow organ irrigation systems are provided, including collapsible and expandable liquid reservoirs, self-supporting liquid containers for liquid reservoirs, and retaining elements for rectal catheters, which may be inflatable or un-inflatable.

18 Claims, 25 Drawing Sheets

(58) Field of Classification Search
CPC .............. A61M 3/0262; A61M 3/0266; A61M 5/1413; A61M 5/1414; A61M 5/1415; A61M 5/1417; A61M 3/0258; A61M 2210/1067; A61M 2210/1064; A61M 3/0295; A61M 39/26; A61B 2017/22037; A61H 2201/0119
See application file for complete search history.

(56) References Cited

U.S. PATENT DOCUMENTS

| | | | | |
|---|---|---|---|---|
| 5,836,907 | A * | 11/1998 | Campbell | A61M 3/0241 604/27 |
| 8,900,184 | B2 | 12/2014 | Gobei | |
| 2010/0018607 | A1 * | 1/2010 | Cuzydlo | A61M 16/186 222/173 |
| 2010/0308133 | A1 * | 12/2010 | Yeh | A61M 3/0262 239/327 |
| 2014/0005602 | A1 | 1/2014 | Andreen et al. | |
| 2014/0163487 | A1 * | 6/2014 | Tout | A61M 3/0258 604/305 |
| 2016/0008533 | A1 * | 1/2016 | Muhammad | A61M 3/0241 604/246 |
| 2016/0339227 | A1 * | 11/2016 | Tsai | A61F 5/451 |

FOREIGN PATENT DOCUMENTS

| | | | | |
|---|---|---|---|---|
| WO | WO-2016007536 | A1 * | 1/2016 | .......... A61M 3/0208 |
| WO | WO 2018/009818 | A1 | 1/2018 | |
| WO | WO 2018/009871 | A1 | 1/2018 | |

* cited by examiner

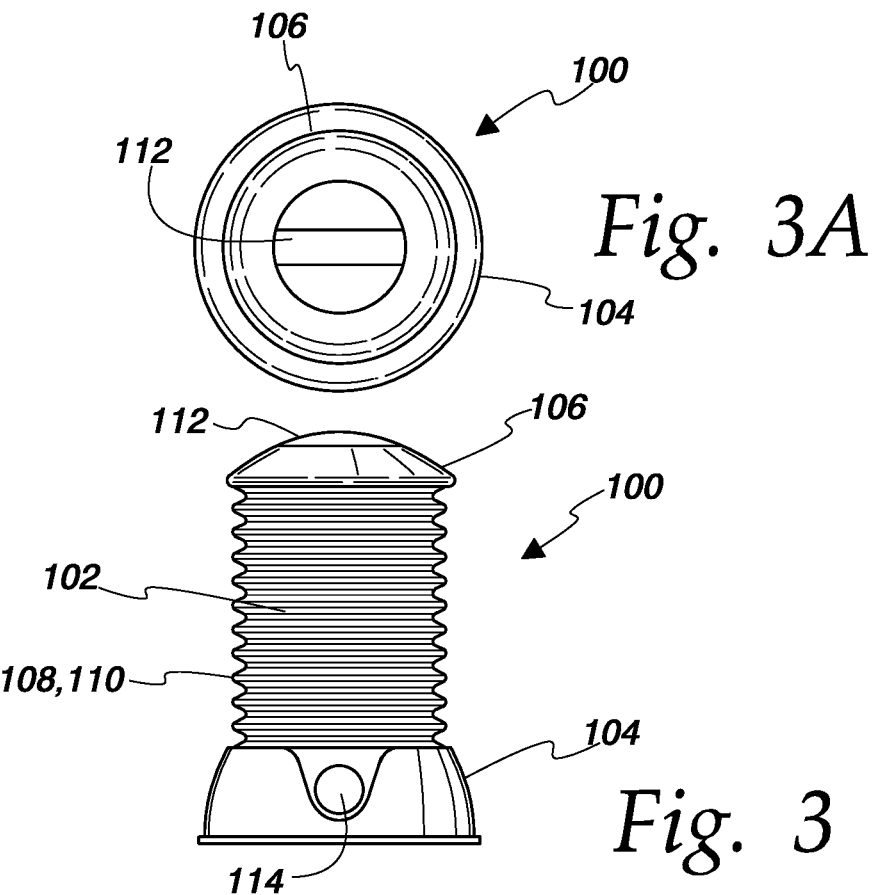
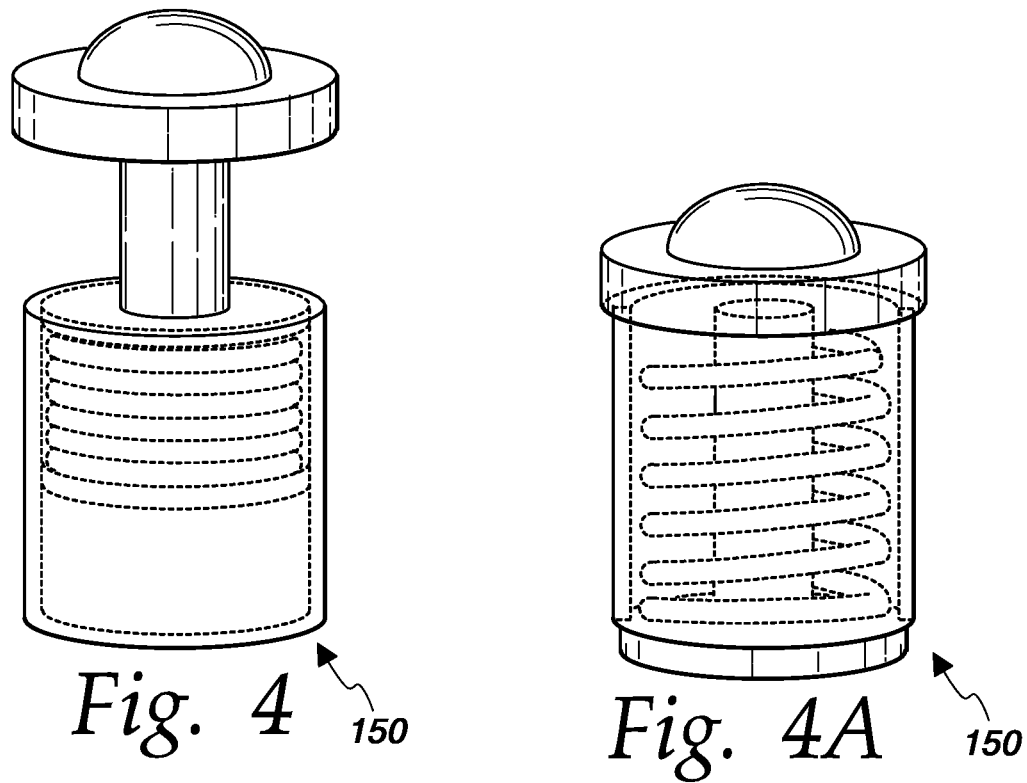

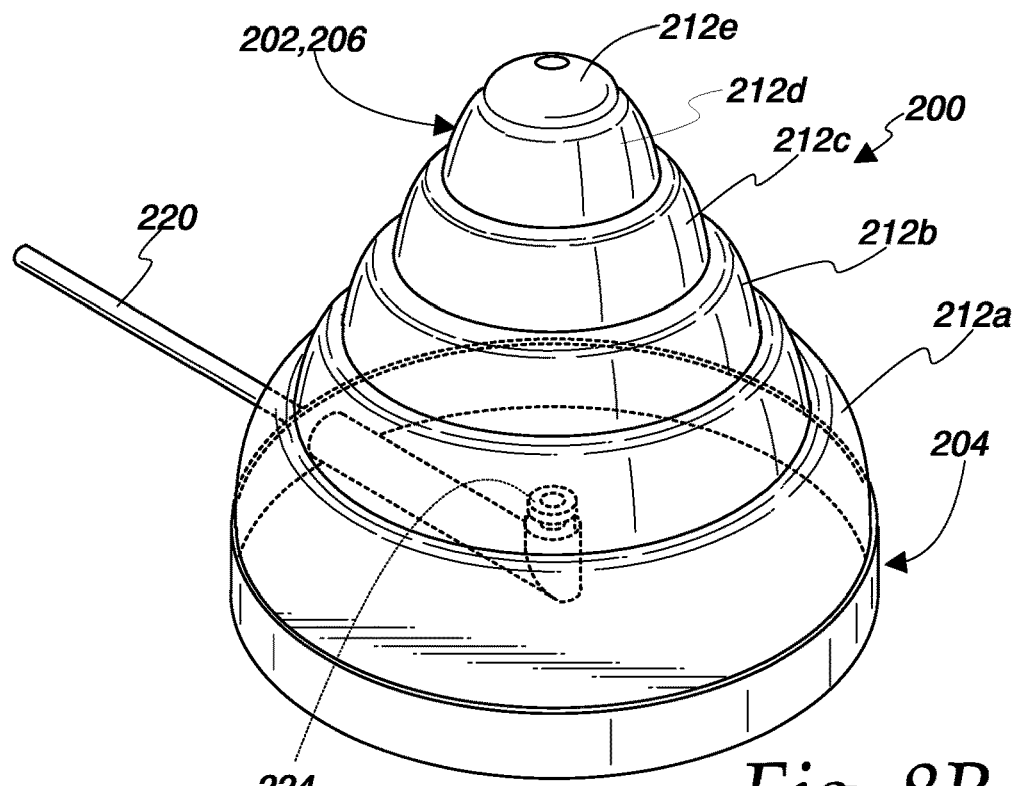
Fig. 8B
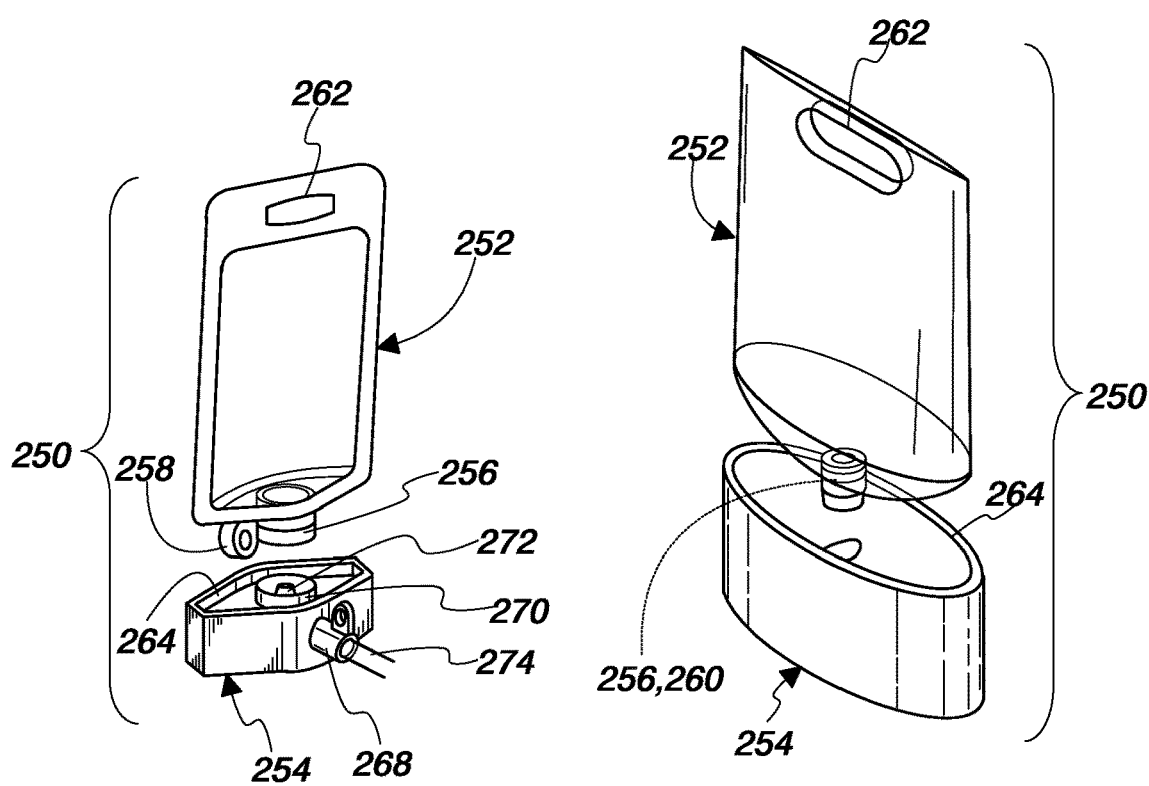
Fig. 9
Fig. 9A

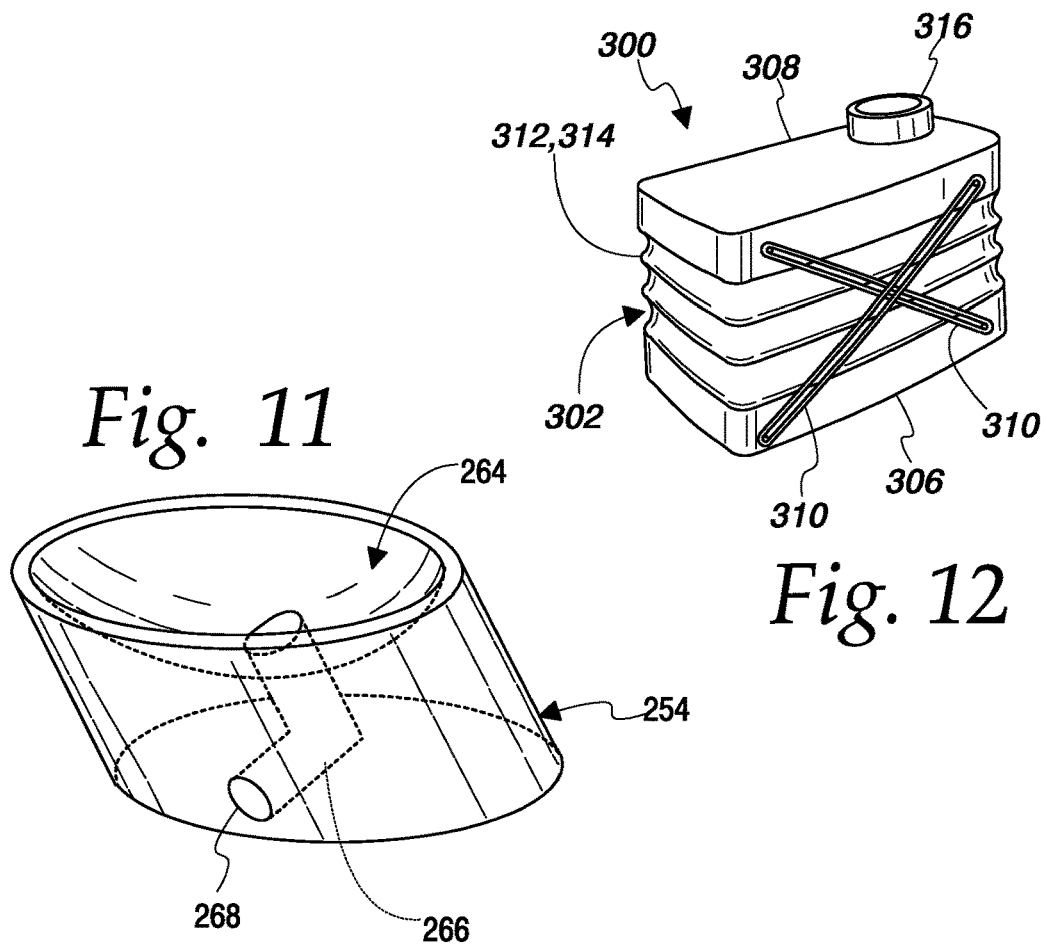
*Fig. 11*
*Fig. 12*
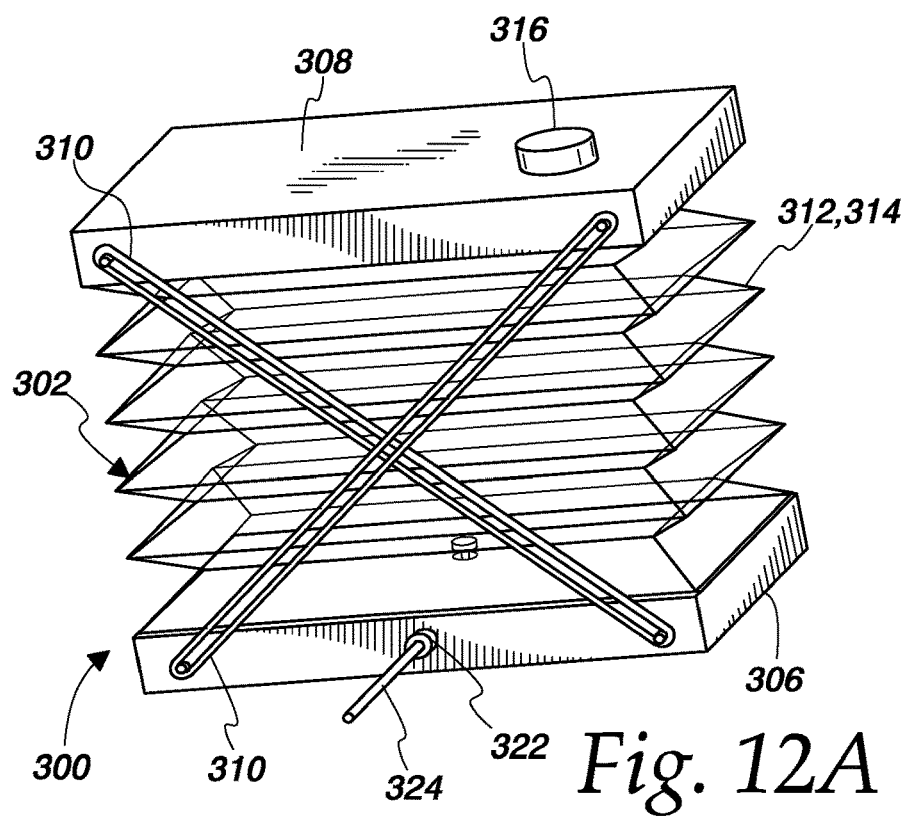
*Fig. 12A*

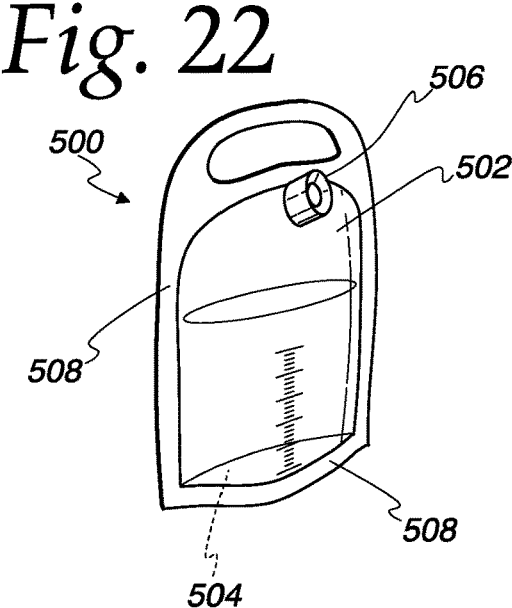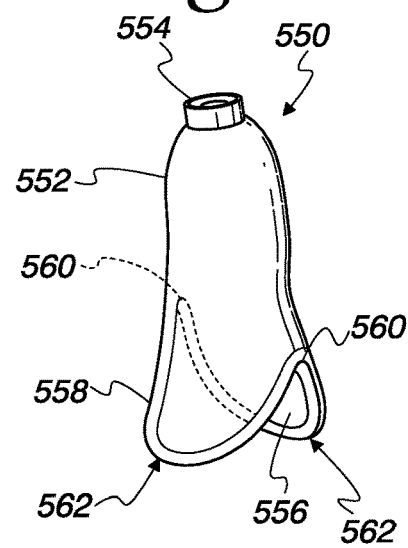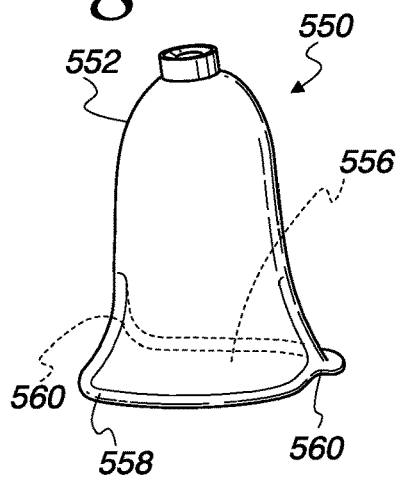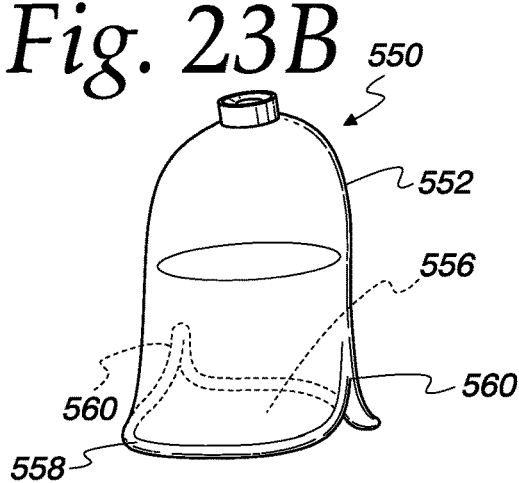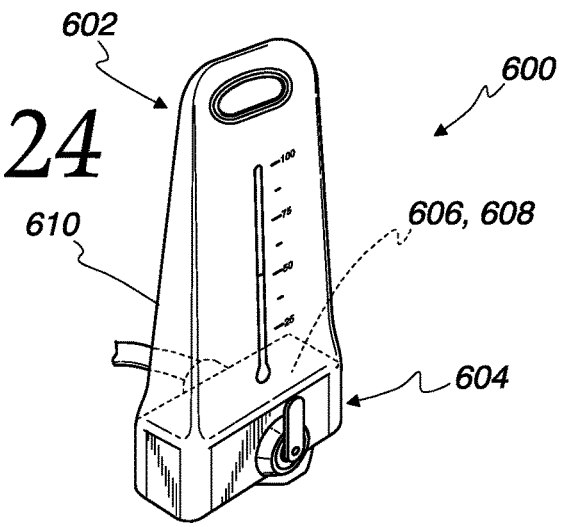

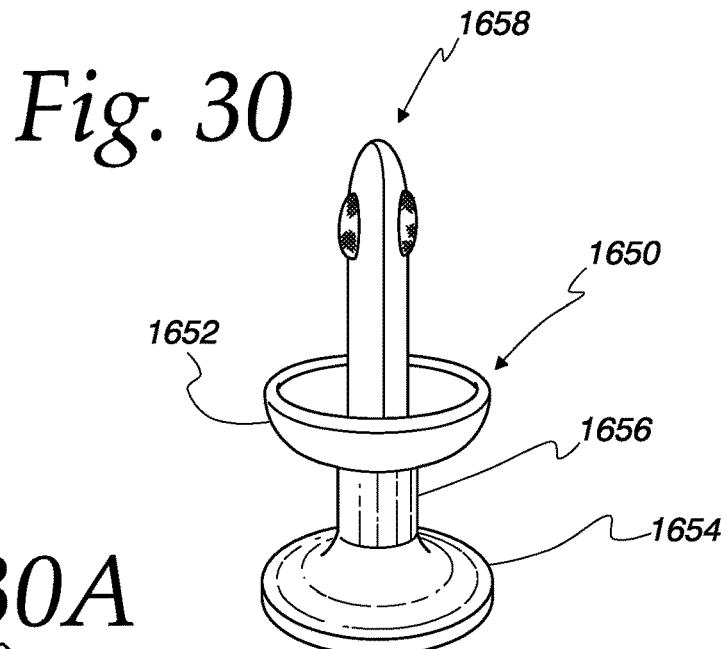
Fig. 30
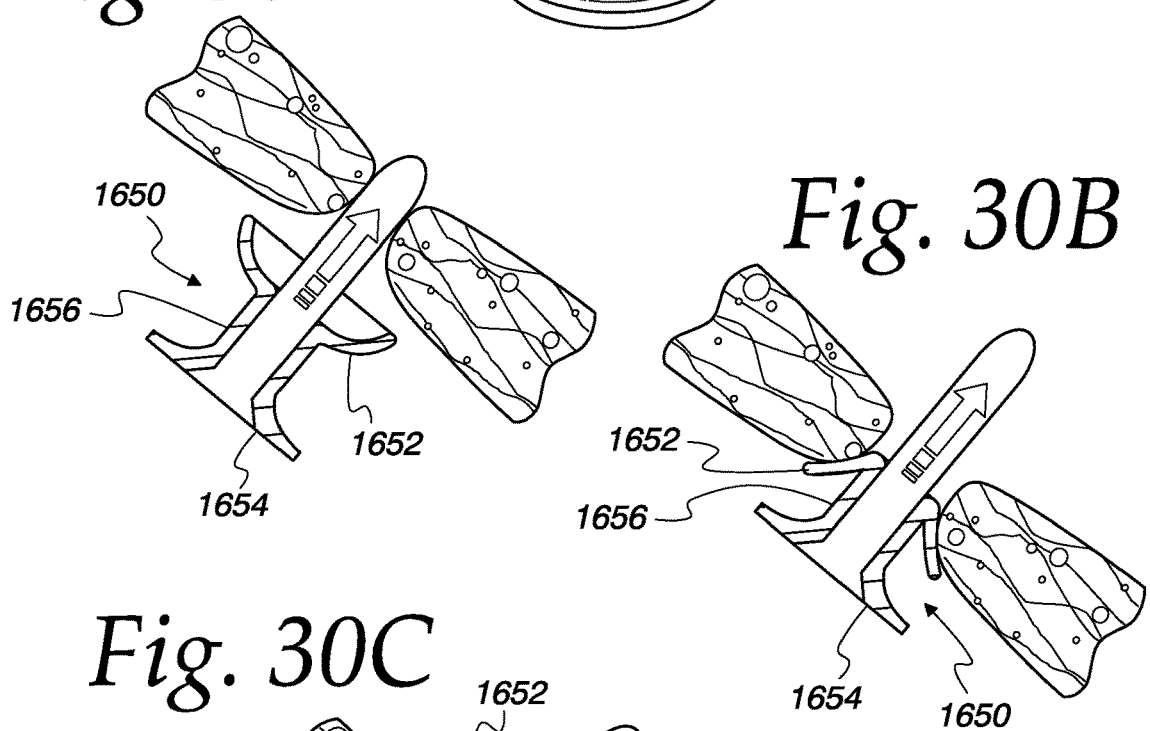
Fig. 30A
Fig. 30B
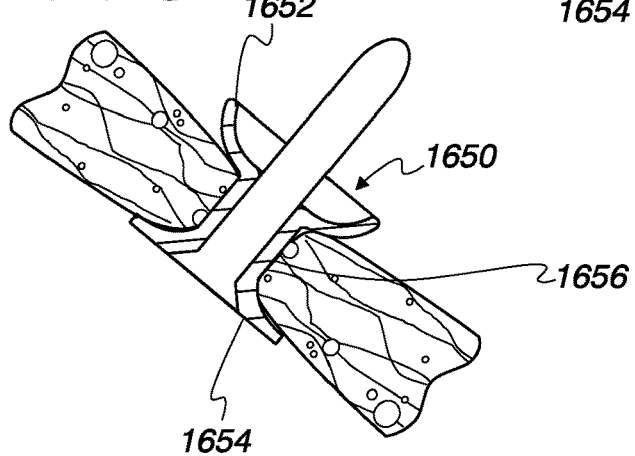
Fig. 30C

HOLLOW ORGAN IRRIGATION SYSTEMS

RELATED APPLICATIONS

This application is a U.S. national stage application of PCT Patent Application Serial No. PCT/US2018/047659, filed Aug. 23, 2018, which claims the benefit of and priority of U.S. Provisional Patent Application Ser. No. 62/549,713, filed Aug. 24, 2017, the contents of which are incorporated by reference herein.

DESCRIPTION

Technical Field

The present disclosure generally relates to hollow organ irrigation devices, systems, and methods. More particularly, the present disclosure relates to liquid reservoirs, catheters, and catheter retaining elements that may be employed in hollow organ irrigation devices, systems, and methods.

BACKGROUND

Hollow organ irrigation is a process by which an individual introduces an irrigant fluid into a hollow organ, such as, for example, the rectum, colon or other sections of the intestines. Trans-anal irrigation ("TAI") is an exemplary hollow organ irrigation process used by individuals who have bowel management issues, such as incontinence, constipation, or other neurogenic bowel dysfunction (NBD). Alternatively, TAI may be used for regular bowel evacuations by individuals who are incapacitated due to illness or other medical conditions or injuries (such as spinal cord injury) and thus lack the mobility to access a toilet. During TAI, water or other lavage liquid is introduced into the rectum and colon through a device positioned in the anus so that feces are flushed and evacuated. This creates pseudo-continence for the patient/user. Furthermore, individuals that are bedridden may develop fecal impaction. Such bowel obstructions may be removed via TAI.

Systems for performing TAI currently on the market allow the user to introduce water into the bowel through a rectal catheter while the user sits on a toilet or a commode/shower chair or lies in a bed. The user introduces an amount of water or other liquid into the bowel (typically 500-700 mL) in order to flush out stool located in the bowel passage. The user typically introduces the water, waits for a period of time and then allows gravity to flush the water and stool out of the body. The rectal catheter may have a retention member such as an inflatable/deflatable balloon or cuff to assist in retention of the catheter during water introduction.

TAI is merely one exemplary type of hollow organ/cavity irrigation, with other examples involving the introduction of an irrigant fluid into other hollow organs (e.g., the stomach and/or intestines) via other bodily openings, including a surgically created opening or stoma. For hollow organ irrigation users, independence, dexterity, and ease of use are important needs that must be addressed by hollow organ irrigation systems and methods.

SUMMARY

There are several aspects of the present subject matter which may be embodied separately or together in the devices, systems, and/or methods described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a liquid reservoir for a hollow organ irrigation system includes a liquid reservoir configured to contain an irrigation liquid and including a sidewall. The liquid reservoir also includes a base associated with a lower portion of the liquid reservoir and a top associated with an upper portion of the liquid reservoir. The sidewall includes a plurality of accordion or concertina pleats configured to expand and collapse in a vertical direction to move the liquid reservoir between a collapsed condition and an expanded condition.

In another aspect, a liquid reservoir for a hollow organ irrigation system includes a liquid reservoir configured to contain an irrigation liquid and including a sidewall. The liquid reservoir also includes a base associated with a lower portion of the liquid reservoir. The sidewall is defined by a plurality of step sections each having a smaller outer dimension than the step section positioned therebelow and configured to expand and collapse in a vertical direction to move the liquid reservoir between a collapsed condition and an expanded condition.

In yet another aspect, a liquid reservoir for a hollow organ irrigation system includes a liquid reservoir configured to contain an irrigation liquid and including a pair of facing sidewalls. The liquid reservoir also includes a base associated with an end of the liquid reservoir, which end includes a port and a removable cap associated with the port, with the base defining a docking formation configured to receive at least a portion of the port when the cap has been removed from the port.

In another aspect, a liquid reservoir for a hollow organ irrigation system includes a liquid reservoir configured to contain an irrigation liquid and including a sidewall. The liquid reservoir also includes a frame having a base associated with a lower portion of the liquid reservoir, a top associated with an upper portion of the liquid reservoir, and a plurality of support struts connecting the base and the top. The frame is movable between an expanded condition in which the top is positioned in vertical alignment with and above the base and a collapsed condition in which the top is rotated out of vertical alignment with the base.

In yet another aspect, a self-supporting liquid container for a liquid reservoir of a hollow organ irrigation system includes a pair of flexible sidewalls each having a perimeter and a flexible bottom surface. A portion of the perimeter of each sidewall is joined to a corresponding portion of the perimeter of the other sidewall, while a bottom edge of the perimeter of each sidewall is joined to a perimeter of the bottom surface, with generally rigid edges being defined at the perimeters of the sidewalls and the perimeter of the bottom edge.

In another aspect, a self-supporting liquid container for a liquid reservoir of a hollow organ irrigation system includes a flexible sidewall having a bottom edge with a pair of diametrically opposed slits. A flexible bottom surface having a perimeter is joined to the bottom edge and the slits of the sidewall, with a generally rigid edge being defined at the bottom edge of the sidewall, at the slits, and at the perimeter of the bottom edge.

In yet another aspect, a self-supporting liquid container for a liquid reservoir of a hollow organ irrigation system includes a pair of flexible sidewalls each having a perimeter and a flexible bottom surface. A portion of the perimeter of each sidewall is joined to a corresponding portion of the perimeter of the other sidewall, while a bottom edge of the perimeter of each sidewall is joined to a perimeter of the bottom surface. The bottom surface includes a plurality of accordion or concertina pleats configured to expand and collapse to move the liquid container between a collapsed condition and an expanded condition.

In another aspect, a retaining element for a catheter of a hollow organ irrigation system includes an expandable member movable between a collapsed condition and an expanded condition, with a plurality of supporting petals associated with the expandable member and configured to increase the structural integrity of the expandable member.

In yet another aspect, a retaining element for a catheter of a hollow organ irrigation system includes an expandable member movable between a collapsed condition and an expanded condition, with a plurality of smaller expandable members spaced about a perimeter of the expandable member.

In another aspect, a retaining element for a catheter of a hollow organ irrigation system includes a pair of cuffs spaced along a central axis of the retaining element, with an expandable member positioned between the cuffs and movable between a collapsed condition and an expanded condition. The cuffs are positioned and configured to limit the expansion of the expandable member in an axial direction.

In yet another aspect, an un-inflatable retaining element is provided for a catheter of a hollow organ irrigation system. The retaining element is configured to be deformed from an initial, large dimension configuration prior to advancement into a hollow organ to a collapsed, small dimension configuration during advancement into the hollow organ and back to the initial configuration upon full advancement of the retaining element into the hollow organ.

In another aspect, an un-inflatable retaining element is provided for a catheter of a hollow organ irrigation system. The retaining element is configured to be deformed from an initial, large dimension configuration prior to advancement into a hollow organ to a collapsed, small dimension configuration during advancement into the hollow organ and to a different large dimension configuration upon full advancement of the retaining element into the hollow organ.

In yet another aspect, an un-inflatable retaining element is provided for a catheter of a hollow organ irrigation system. The retaining element is configured to be deformed from an initial, small dimension configuration prior to and during advancement into a hollow organ to an expanded, large dimension configuration upon full advancement of the retaining element into the hollow organ.

In another aspect, an un-inflatable retaining element is provided for a catheter of a hollow organ irrigation system. The retaining element is configured to be deformed from an initial equilibrium state prior to advancement into a hollow organ to a different equilibrium state upon full advancement of the retaining element into the hollow organ.

In yet another aspect, an un-inflatable retaining element for a catheter of a hollow organ irrigation system comprises a sealed pouch filled with a compressible fluid.

In another aspect, an un-inflatable retaining element for a catheter of a hollow organ irrigation system includes a body portion extending between an upper end and a lower end, with an upwardly extending flange portion associated with the lower end of the body portion. The body portion is pivotal about its upper end between a compressed condition and an expanded condition.

BRIEF DESCRIPTION OF THE DRAWINGS

FIG. 3 is a front elevational view of another embodiment of a liquid reservoir according to an aspect of the present disclosure;

FIG. 3A is a top plan view of the liquid reservoir of FIG. 3;

FIG. 4 is a front perspective view of an exemplary valve that may be incorporated into a liquid reservoir of the present disclosure, with the valve shown in an open condition;

FIG. 4A is a front perspective view of the valve of FIG. 4, with the valve shown in a closed condition;

FIG. 8B is a rear perspective view of the liquid reservoir of FIG. 8A, with the container in an expanded condition;

FIG. 9 is an exploded, front perspective view of another embodiment of a liquid reservoir according to an aspect of the present disclosure;

FIG. 9A is an exploded, rear perspective view of the liquid reservoir of FIG. 9;

FIG. 11 is a front perspective view of a base of the liquid reservoir of FIG. 9;

FIG. 12 is a rear perspective view of another embodiment of a liquid reservoir according to an aspect of the present disclosure;

FIG. 12A is a front perspective view of the liquid reservoir of FIG. 12;

FIG. 22 is a front perspective view of a container that may be incorporated into a liquid reservoir according to the present disclosure;

FIG. 23 is a front perspective view of another embodiment of a container that may be incorporated into a liquid reservoir according to the present disclosure, with the container shown in a partially collapsed condition;

FIG. 23A is a front perspective view of the container of FIG. 23, with the container shown in an expanded condition; and FIG. 23B is a front perspective view of the container of FIG. 23, with the container shown in an expanded condition and filled with a liquid;

FIG. 24 is a front perspective view of another embodiment of a liquid reservoir according to the present disclosure;

FIG. 30 is a front perspective view of a portion of another embodiment of a catheter according to an aspect of the present disclosure;

FIGS. 30A-30C illustrate a retaining element of the catheter of FIG. 30 as it is advanced into a hollow organ;

DETAILED DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

The present disclosure includes various components that may be employed in hollow organ irrigation systems, devices, and methods. The components include liquid reservoirs, catheters, and retaining/sealing elements. The hollow organ irrigation components disclosed herein may be incorporated into most hollow organ irrigation (including TAI) systems, which may be mechanical or electric pump controlled systems or gravity or compression feed systems.

A. Exemplary Hollow Organ Irrigation System and Method of Operation

Figure 1:
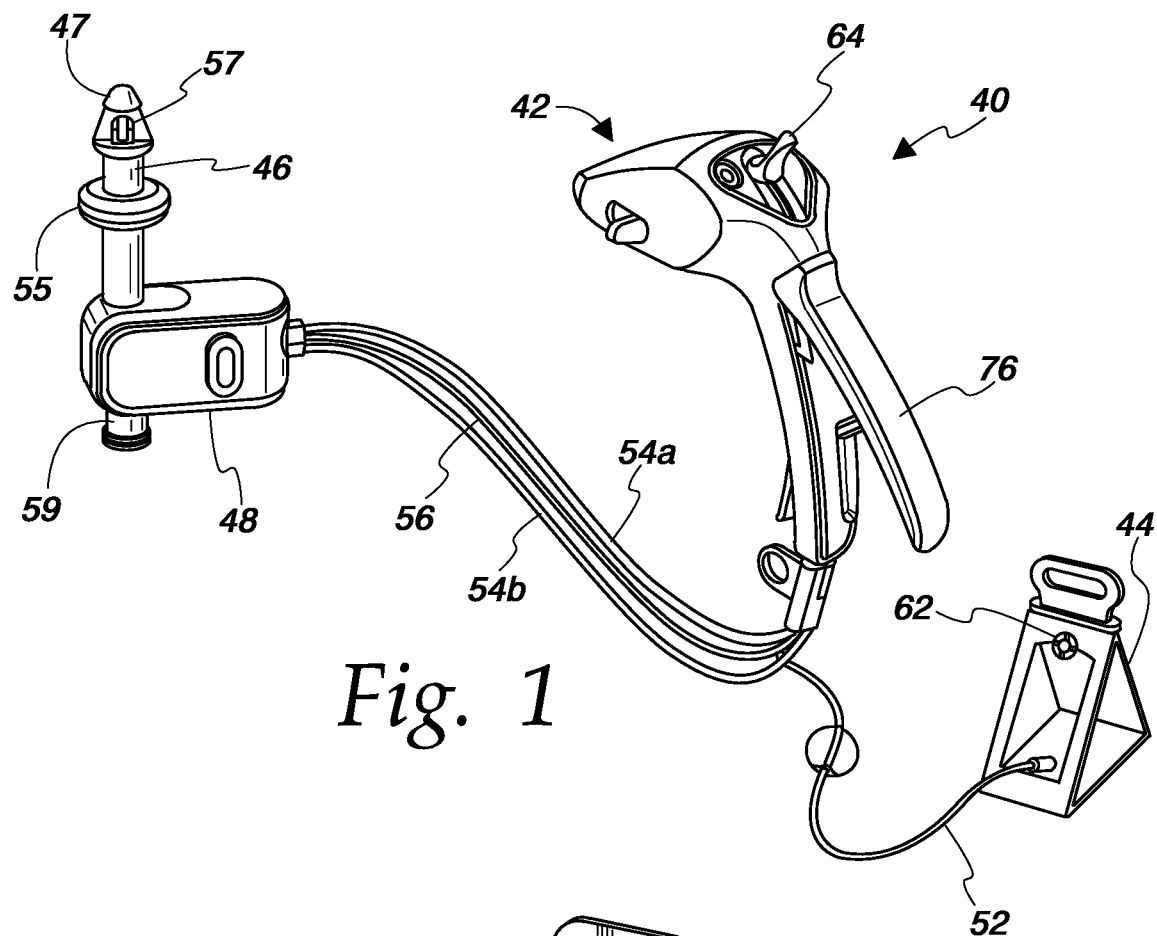
FIG. 1 is a front perspective view of components of an exemplary hollow organ irrigation system.
Figure 2:
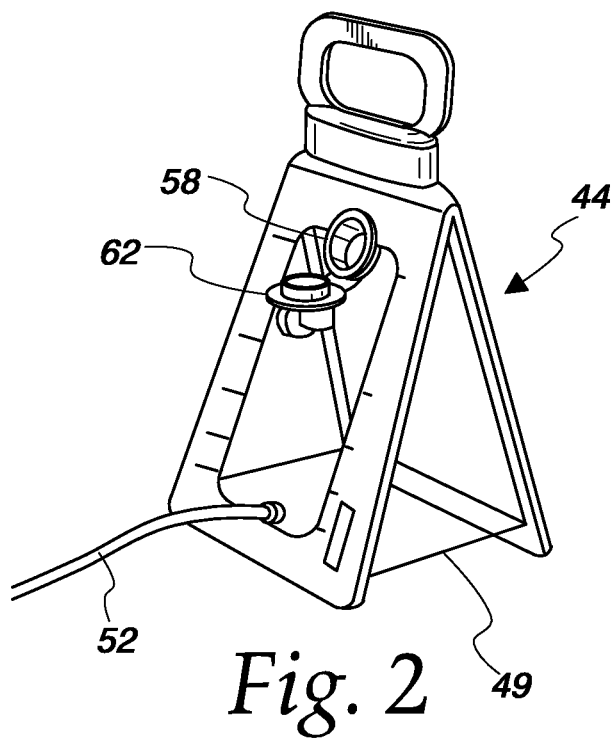
FIG. 2 is an enlarged, front perspective view of a liquid reservoir of the system of FIG. 1.

FIGS. 1 and 2 illustrate an exemplary mechanically controlled hollow organ irrigation system indicated in general at 40 in FIG. 1. The hollow organ irrigation system 40 is shown herein mainly to provide background and context for the various hollow organ irrigation components and devices disclosed herein. A full description of a mechanical system of the type shown in FIG. 1 may be found in PCT Patent Application Serial No. PCT/US17/41127, filed Jul. 7, 2017, which is hereby incorporated herein by reference. A description of an electronically controlled system in which the components and devices of this disclosure may be employed is described in PCT Patent Application Serial No. PCT/US17/41205, filed Jul. 7, 2017, which is hereby incorporated herein by reference.

It should be understood that the hollow organ irrigation components and devices disclosed are not limited to incorporation into any particular hollow organ irrigation system, including the hollow organ irrigation system 40 of FIG. 1, but may be incorporated into any suitable hollow organ irrigation system. Additionally, the various hollow organ irrigation components and devices described herein may be individually incorporated into a given hollow organ irrigation system or a plurality of hollow organ irrigation components and devices according to the present disclosure may be incorporated into a given hollow organ irrigation system (e.g., one liquid reservoir and one catheter), with there being no specific limitation on the different combinations of hollow organ irrigation components and devices that may be incorporated into a given hollow organ irrigation system. For illustrative purposes, the hollow organ irrigation system 40 of FIG. 1 and the various other hollow organ irrigation devices and components of the present disclosure will be described in a TAI context (e.g., with the TAI system having a rectal catheter that is particularly configured for advancement into the rectum), but it should be understood that the systems, devices, and components described herein may be employed in other hollow organ irrigation/hollow cavity contexts, such as irrigation of the stomach or the intestines using a catheter advanced into the stomach/intestines via a stoma.

Referring to FIG. 1, the TAI system 40 includes a pump controller, indicated in general at 42, an irrigant or lavage liquid reservoir 44, a rectal catheter 46, and a catheter hub 48. A single segment of tubing 52 runs between the liquid reservoir 44 and the pump controller 42. A pair of tubing segments 54a and 54b run from the pump controller 42 to the catheter hub 48. One tubing segment 54a is in communication with a retaining element 55 of the rectal catheter 46 and allows the flow of a fluid (e.g., water or air) to and from the retaining element 55 for inflation and deflation thereof. The other tubing segment 54b is in communication with openings 57 in the top or tip or head 47 of the rectal catheter 46 and delivers irrigant pumped from the reservoir 44 to the catheter 46 and out of the openings 57. A sheath 56 containing a waste drain valve line also runs between the controller 42 and the catheter hub 48. In one embodiment, the rectal catheter 46 is disposable and is attached in a removable fashion to the durable or reusable hub 48. The rectal catheter 46 may be used by a patient either on a toilet or the like or in a bed setting. As will be described in greater detail herein, the rectal catheter may be variously configured without departing from the scope of the present disclosure.

The liquid reservoir 44 of the TAI system 40 is illustrated in greater detail in FIG. 2. In the illustrated embodiment, the reservoir 44 houses a liquid tank or container 49 having a fill opening 58 with a removable fill cap 62. As will be described in greater detail herein, the liquid reservoir may be variously configured without departing from the scope of the present disclosure.

In use, before the top end of the rectal catheter 46 is inserted into the rectum of the user/patient, the system 40 is primed in order to remove the air from the system 40. This may be achieved by moving a toggle switch 64 of the pump controller 42 to a priming configuration. In the priming configuration, the reservoir 44 is placed in fluid communication with the tubing segment 54b and, thus, the catheter head openings 57 to remove air from the system 40 by operation of the system pump.

With the catheter tubing primed, the tapered head 47 and deflated or collapsed retaining element 55 of the catheter 46 are safely inserted into the rectum of the user/patient. Toggle switch 64 of the controller 42 is toggled to the place the system 40 in a configuration for inflating or otherwise expanding the retaining element 55. In this configuration, the reservoir 44 is placed in fluid communication with the tubing segment 54a to delivery liquid (e.g., water) to the retaining element 55. As a result, when the user squeezes the controller lever 76, liquid is pumped from the liquid container 49, through the tubing segments 52 and 54a, and into the retaining element 55 so as to inflate it.

With the retaining element 55 of the catheter 46 inflated, the user is now ready to irrigate the rectum. The user toggles switch 64 of the controller 42 to place the system 40 into a third position for irrigation. In this configuration, the reservoir 44 is placed in fluid communication with the tubing segment 54b for delivering liquid to the catheter 46 and out of the openings 57 in the tip 47 of the catheter 46. As a result, when the user squeezes the controller lever 76, liquid is pumped from the reservoir 44, through the tubing segments 52 and 54b, and out of the openings 57 and into the rectum of the patient. The retaining element 55 maintains the tip 47 of the catheter 46 in the rectum, while preventing the irrigant from draining out of the rectum.

After the appropriate volume of irrigant has been introduced into the rectum, it is allowed to irrigate the rectum for a defined period of time. Thereafter, the user performs two actions. First, switch 64 of the controller 42 is toggled to a flush position. In this configuration, the liquefied fecal and other waste flows into the openings 57 of the catheter tip 47 and through a drain passage 59 of the catheter 46, where it exits into a toilet, waste collection bag, or other waste disposal destination or device.

When the user is confident that they have completed their TAI procedure, the catheter 46 is removed from the rectum. This is done by moving the toggle switch 64 into a retaining element deflation position in which the retaining element 55 is deflated. Once the retaining element 55 is deflated, the user can then safely remove the catheter 46 from the rectum, disconnect the catheter 46 from the hub 48 and dispose of the catheter 46 hygienically.

FIGS. 3-24 illustrate various embodiments of liquid reservoirs (and/or components thereof) that may be used in a hollow organ irrigation system, device, or method. FIGS. 25-38A illustrate various embodiments of catheters (and/or components thereof) that may be used in a hollow organ irrigation system, device, or method.

B. Alternative Embodiments of a Liquid Reservoir

FIGS. 3 and 3A illustrate an irrigant or liquid reservoir 100 that includes a liquid container 102, a base 104, and a top or lid 106. The base 104 and the top 106 may be fixedly secured to the liquid container 102 or may be detachably associated with the liquid container 102.

The liquid container 102 has a sidewall 108 extending between the base 104 and the top 106 and defining an open or hollow interior for containing an amount of irrigant or irrigation liquid. In the illustrated embodiment, the sidewall 108 has a generally tubular or cylindrical configuration, but it should be understood that the sidewall 108 may be differently shaped (e.g., having a square or rectangular footprint) without departing from the scope of the present disclosure.

At least a portion of the sidewall 108 of the liquid container 102 includes multiple accordion or concertina pleats 110, which are expandable and compressible in a vertical direction to move the liquid container 102 between a collapsed or compact condition (having a relatively small height) and the expanded condition of FIG. 3 (having a relatively great height). In the collapsed condition, the pleats 110 remain vertically stacked above each other (as in the expanded condition of FIG. 3), but each pleat 110 collapses onto itself to have a lesser height than in the expanded condition, thereby giving the entire liquid container 102 a decreased height. To facilitate movement of the liquid container 102 between its collapsed and expanded conditions, it may be advantageous for the sidewall 108 to be formed of a semi-rigid material, which is sufficiently rigid to support itself in the expanded condition, but sufficiently deformable at the pleats 110 to be moved to the collapsed condition.

In the collapsed condition, the volume defined by the sidewall 108 is relatively small (e.g., defining a volume that is smaller than the volume of liquid required during a typical TAI procedure), in which case the collapsed condition may be considered a storage or transport configuration, while the liquid container 102 may be placed into the expanded condition of FIG. 3 for use. The top 106 may include a formation or handle 112 that may be gripped (along with a portion of the base 104) for moving the base 104 toward and away from the top 106, thereby moving the liquid container 102 between the collapsed and expanded conditions.

In the illustrated embodiment, the base 104 defines a cavity that is sufficiently sized to receive the entire liquid container 102 in the collapsed condition. The cavity of the base 104 may also receive a portion of the top 106 in the collapsed condition or, alternatively, the top 106 may rest upon the upper end of the base 104, with the liquid container 102 being completely enclosed by the combination of the base 104 and the top 106 in either case. The base 104 and the top 106 may be formed of relatively rigid materials to support and protect the liquid container 102 during storage and/or transportation. In other embodiments, all or a portion of the sidewall 108 may remain exposed between the base 104 and the top 106 when the liquid container 102 is in its collapsed condition.

All or a portion of the top 106 may be removable to allow the liquid container 102 to be filled via an upper opening or port defined in the liquid container 102 (not illustrated). If the top 106 is provided with a handle 112, the handle 112 may be manipulated to remove a portion of the top 106 for filling the liquid container 102 (e.g., by rotating the handle 112 to unscrew a portion of the top 106 from the remainder of the top 106 or by pulling two portions of the top 106 apart to overcome a friction fit). In other embodiments, the liquid container 102 may omit an upper opening or port and instead include only a lower opening or port (not illustrated) for filling and emptying the liquid container 102.

The lower port or opening of the liquid container 102 is in fluid communication (e.g, by a conduit defined in the base 104) with a port 114 of the base 104, with the port 114 being configured to accommodate a tubing segment or the like leading to other components of the system (e.g., a pump controller, as in FIG. 1). FIGS. 4 and 4A illustrate an exemplary valve 150 that may be incorporated into the lower port of the liquid container 102 or into the base 104 for selectively allowing and preventing fluid flow through the port 114, with FIG. 4 showing the valve 150 in an open condition for allowing fluid flow and FIG. 4A showing the valve 150 in a closed condition for preventing fluid flow. The valve 150 may be actuated by another component of the TAI system (e.g., by a pump controller, in the embodiment of FIG. 1) or may be directly manually manipulated by a user or operator. In one embodiment, the valve 150 is automatically opened upon the liquid container 102 being associated to the base 104 and automatically closed upon the liquid container 102 being detached from the base 104. While FIGS. 4 and 4A illustrate a spring-loaded valve 150 that is biased to a closed condition, it should be understood that the configuration of the valve incorporated into the liquid container 102 or the base 104 may vary without departing from the scope of the present disclosure.

In one exemplary method of using the liquid reservoir 100, the liquid container 102 may be moved from its expanded condition to its collapsed condition (or at least to a less expanded condition) to force irrigant in the liquid container 102 out of the port 114 of the base 104 and to a rectal catheter during a TAI procedure. In another exemplary method of using the liquid reservoir 100, the liquid container 102 may remain in an at least partially expanded condition during a TAI procedure, with a pump or the like drawing irrigant out of the liquid container 102 via the port 114 of the base 104 without moving the sidewall 108 to a more collapsed condition.

FIGS. 5-8B illustrate a variation of the liquid reservoir 100 of FIGS. 3 and 3A and individual components thereof. In the embodiment of FIGS. 5-8B, a liquid reservoir 200 is provided with a liquid container 202 and a base 204, while omitting a top or lid (as in FIGS. 3 and 3A). The liquid container 202 is individually shown in FIGS. 6 and 6A, while the base 204 is individually shown in FIG. 7.

The liquid reservoir 202 has a sidewall 206 extending between a lower end 208 and an upper end 210 (FIG. 6) and defining an open or hollow interior for containing an amount of irrigant or liquid. In the illustrated embodiment, the sidewall 206 has a generally conical configuration, but it should be understood that the sidewall 206 may be differently shaped (e.g., having a pyramidal shape) without departing from the scope of the present disclosure.

The sidewall 206 is formed by a plurality of step sections 212a-212e of progressively smaller outer dimension or diameter from top to bottom. In the illustrated embodiment, the sidewall 206 is defined by five step sections, but it should be understood that the sidewall 206 may include a different number of step sections without departing from the scope of the present disclosure. The outer diameter or dimension of each step section is slightly larger than the inner diameter or dimension of the step section directly beneath it, which allows each step section to sit upon the step section directly beneath it, providing an overall stair-stepped construction to the liquid container 202 in its expanded condition (FIGS. 5, 6, and 8B).

Some or all of the step sections 212a-212e may include a generally vertical riser segment or portion joined by generally horizontal tread segment or portion. The step sections 212a-212e may be formed of a semi-rigid material that is sufficiently rigid to allow the step sections 212a-212e to be stacked upon each other in the expanded condition, while having a degree of flexibility to allow the junctions between the riser and tread segments to form flexible hinges. Thus, while the outer diameter or dimension of an individual step section is slightly larger than the inner diameter or dimension of the step section directly beneath it, the flexible hinges allow each step section to be pressed or collapsed downwardly into the step section directly beneath it. The flexible hinges, thus, allow the step sections 212a-212e to be moved from their expanded condition to a partially (FIG. 5A) or fully (FIGS. 6A, 8, and 8A) collapsed condition. In the fully collapsed condition, all of the step sections 212a-212e are collapsed into a common plane, with each being nested within the step section it had previously been positioned directly above in the expanded condition. This is in contrast to the embodiment of FIGS. 3 and 3A, in which the pleats 110 collapse on top of each other in a vertical stack, rather than collapsing into a common plane.

It should be understood that flexible hinges are not the only possible approach for providing a stair-stepped expanded configuration that collapses into a common plane. For example, some or all of the step sections 212a-212e may be provided with tread segments having mating grooves and flanges. The grooves of a step section may be aligned with the flanges of an adjacent step section, which allows the tread segments of the two step sections to be moved vertically past each other, followed by the step sections being rotated relative to each other to misalign the grooves and flanges, thereby allowing the tread segment of one step section to be seated upon the tread segment of the other step section as a stack. In yet another embodiment, adjacent step sections may be provided with mating threads, which allows relative rotation of the two step sections to selectively expand and collapse them. Other mechanisms for expanding and collapsing the step sections 212a-212e may also be employed without departing from the scope of the present disclosure.

Figure 5:
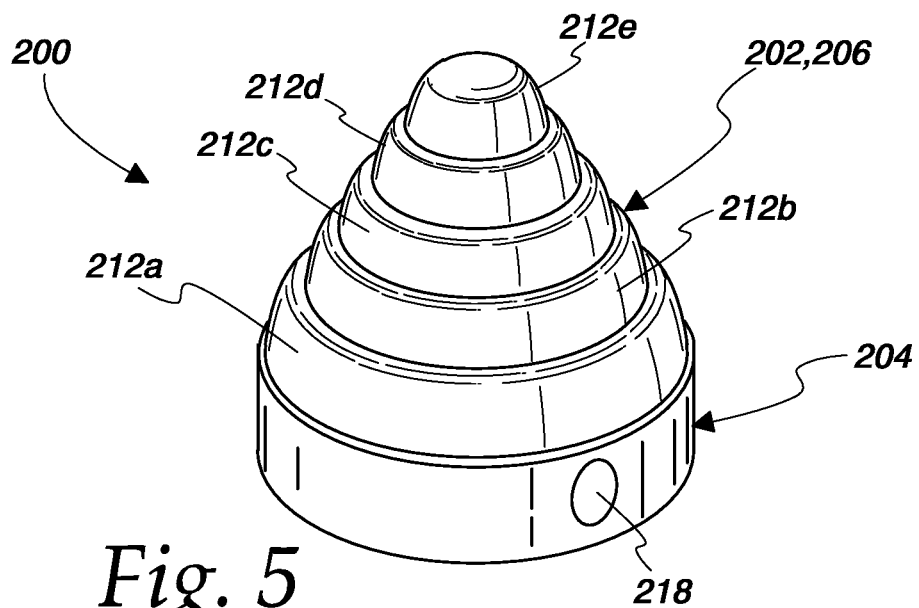
FIG. 5 is a front perspective view of a base and container of another embodiment of a liquid reservoir according to an aspect of the present disclosure, with the container shown in an expanded condition.
Figure 5A:
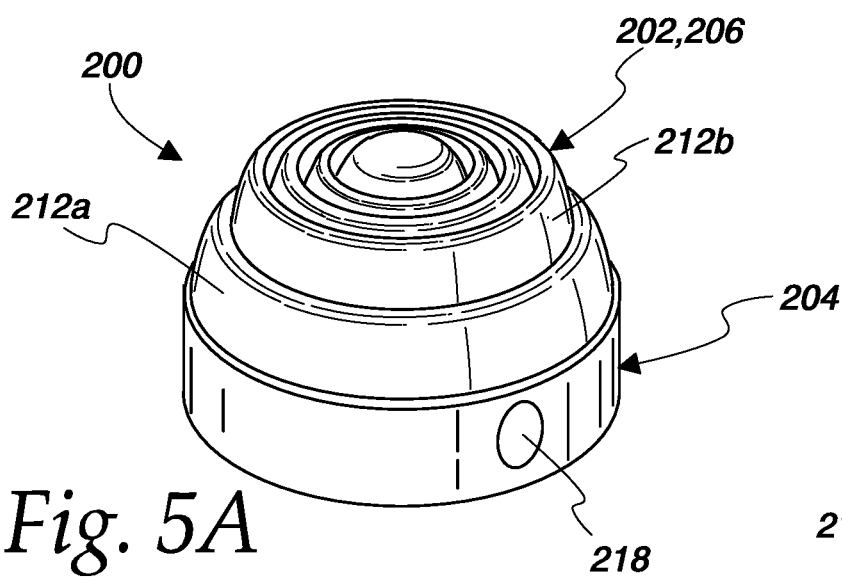
FIG. 5A is a front perspective view of the base and container of FIG. 5, with the container shown in a partially collapsed condition.
Figure 6:
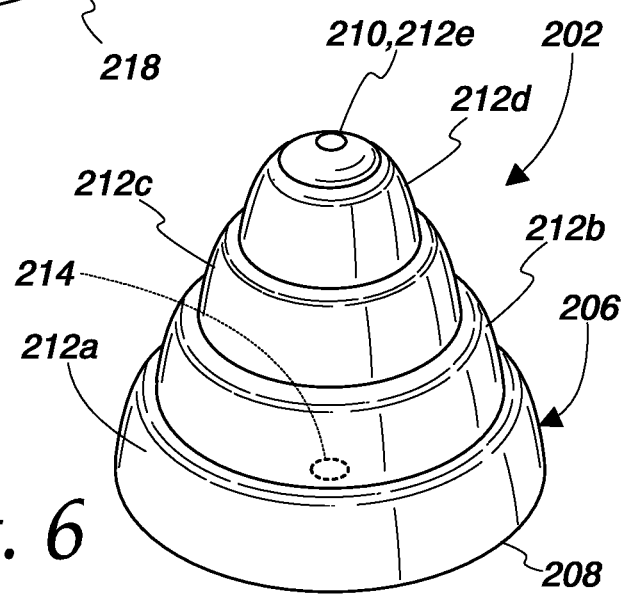
FIG. 6 is a front perspective view of the container of FIG. 5, in an expanded condition.
Figure 6A:
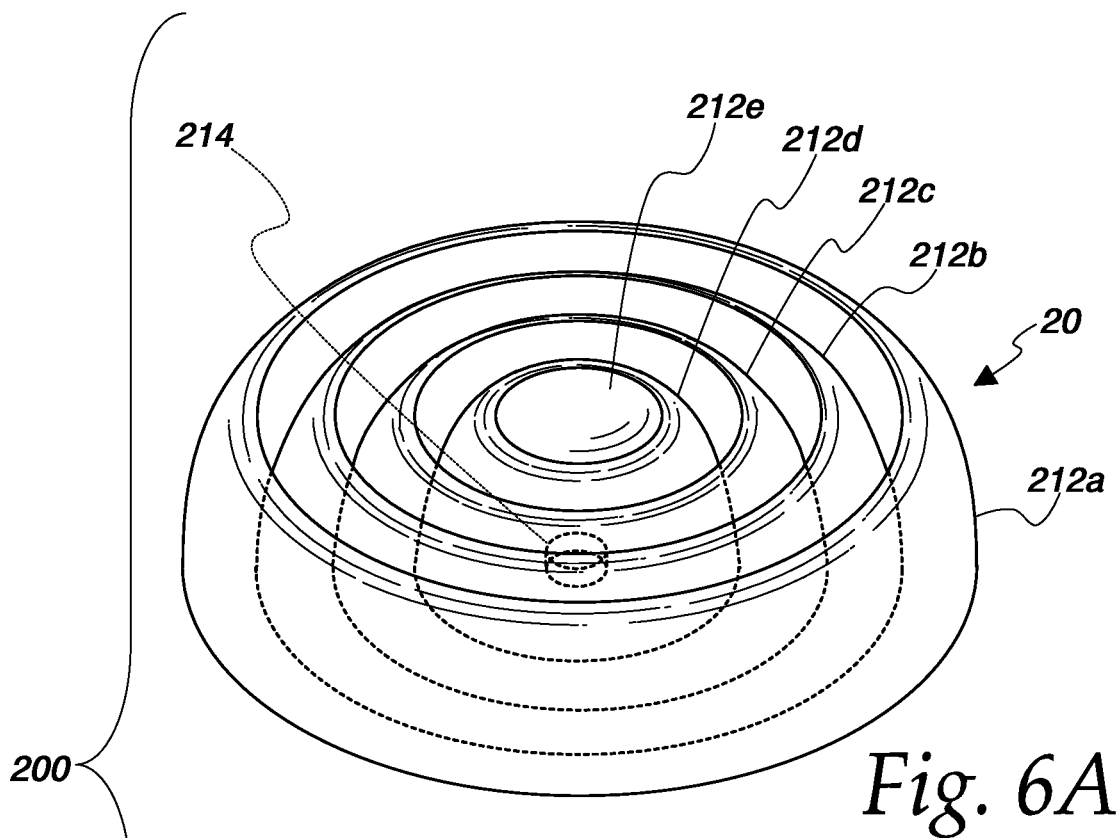
FIG. 6A is a front perspective view of the container of FIG. 5, in a collapsed condition.
Figure 7:
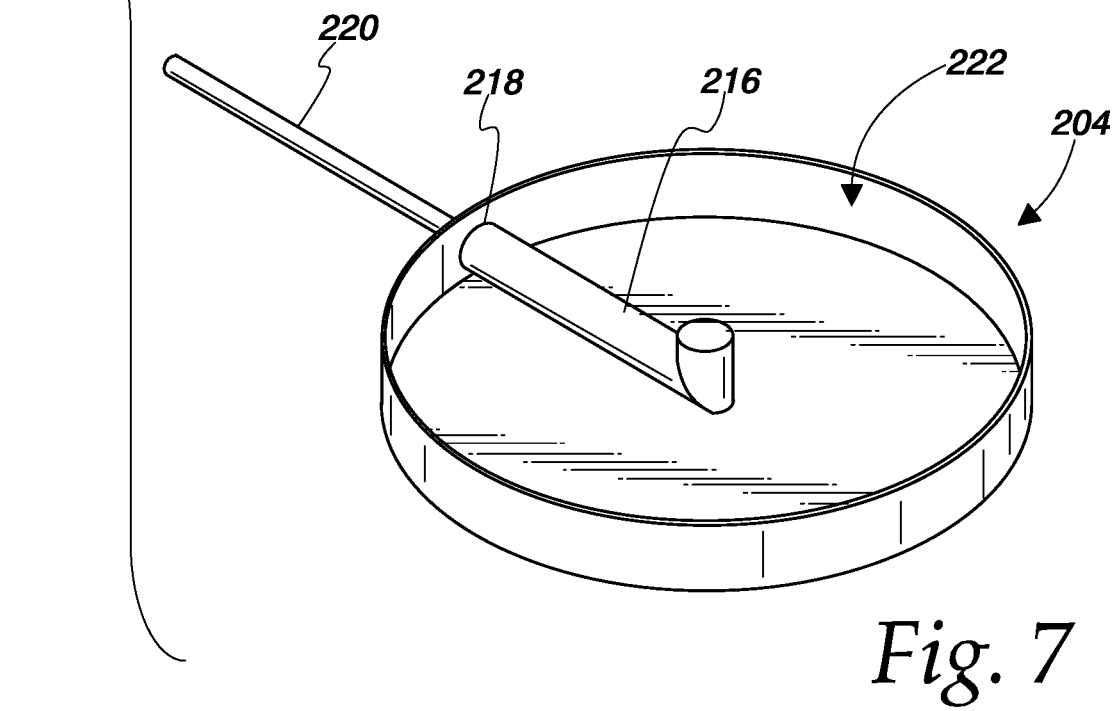
FIG. 7 is a rear perspective view of the base of FIG. 5.
Figure 8:
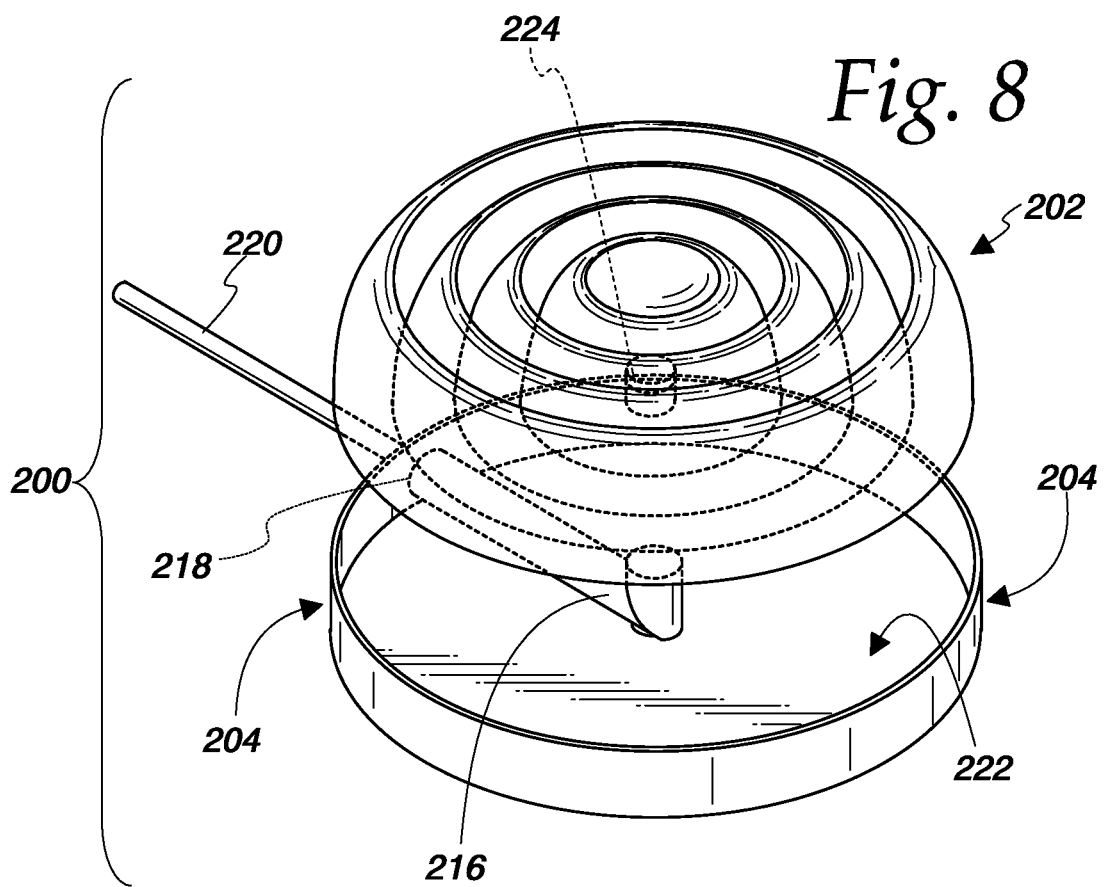
FIG. 8 is an exploded, rear perspective view of a liquid reservoir incorporating the base and container of FIG. 5.
Figure 8A:
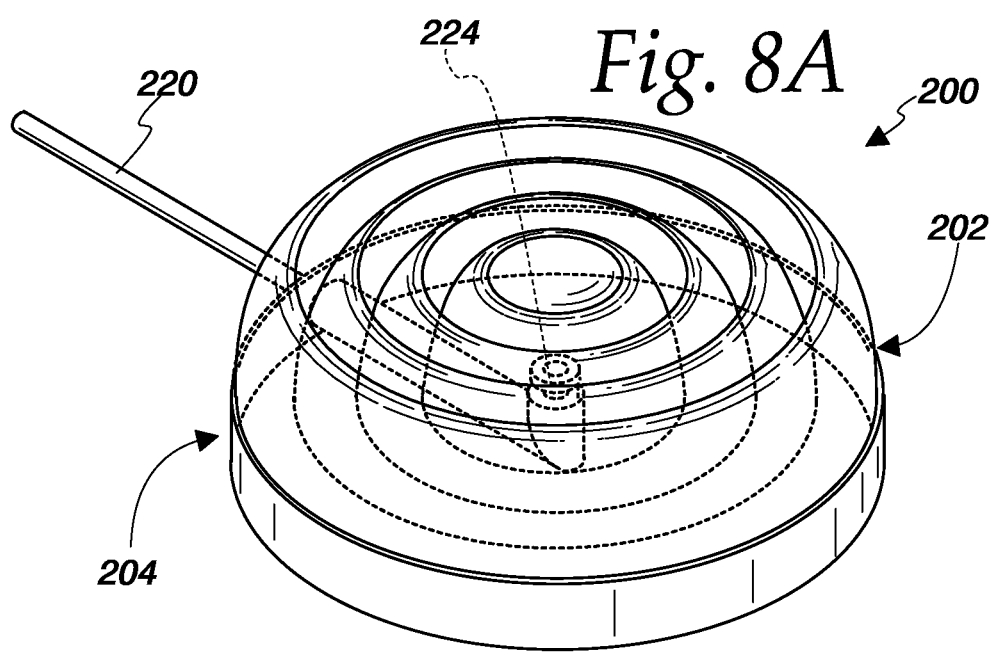
FIG. 8A is an assembled, rear perspective view of the liquid reservoir of FIG. 8, with a container of the liquid reservoir in a collapsed condition.

The bottom step section 212a may be provided with a port or opening 214 that is in fluid communication (e.g., by a conduit 216 defined in the base 204, as in FIGS. 7 and 8) with a port 218 of the base 204 (FIGS. 5 and 5A). The port 218 of the base 204 may be configured to accommodate a tubing segment 220 (FIGS. 7-8B) or the like leading to other components of the TAI system (e.g., a pump controller, as in FIG. 1). The base 204 defines a cavity 222 receiving a portion of the bottom step section 212a, with FIGS. 8 and 8A showing the liquid container 202 being advanced into the base 204. The liquid container 202 may be removably associated with the base 204 or may be fixedly secured thereto. While FIGS. 8 and 8A show the liquid container 202 being advanced into the base 204 in its collapsed condition and then moved to its expanded condition (FIG. 8B), it is also within the scope of the present disclosure for the liquid container 202 to be advanced into the base in its expanded condition. The volume defined by the liquid container 202 may be smaller than the volume of liquid required during a typical TAI procedure, such that the liquid container 202 must be expanded and filled while connected to the base 204 if the liquid container 202 is associated to the base 204 in its collapsed condition. In this case, the liquid container 202 may be provided with a second port for filling the liquid container 202 in the expanded condition. On the other hand, if the liquid container 202 is associated to the base 204 in its expanded condition, it may be filled with irrigant prior to associating the liquid container 202 and the base 204.

A valve 224, such as a valve 150 of the type shown in FIGS. 4 and 4A, may be incorporated into port 214 of the liquid container 202 (as in FIGS. 8-8B) or into the conduit 216 or the port 218 of the base 204 to selectively allow and prevent fluid flow therethrough. In one embodiment, the valve 224 automatically opens upon the liquid container 202 being advanced into the base 204 and automatically closes upon the liquid container 202 being removed from the base 204.

As in the embodiment of FIGS. 3 and 3A, in one exemplary method of using the liquid reservoir 200, the liquid container 202 may be moved from its expanded condition to its collapsed condition (or at least to a less expanded condition) to force irrigant in the liquid container 202 out of the port 218 of the base 204 and to a rectal catheter during a TAI procedure. In another exemplary method of using the liquid reservoir 200, the liquid container 202 may remain in an at least partially expanded condition during a TAI procedure, with a pump or the like drawing irrigant out of the liquid container 200 via the port 218 of the base 204 without moving the sidewall 206 to a more collapsed condition.

Figure 9B:
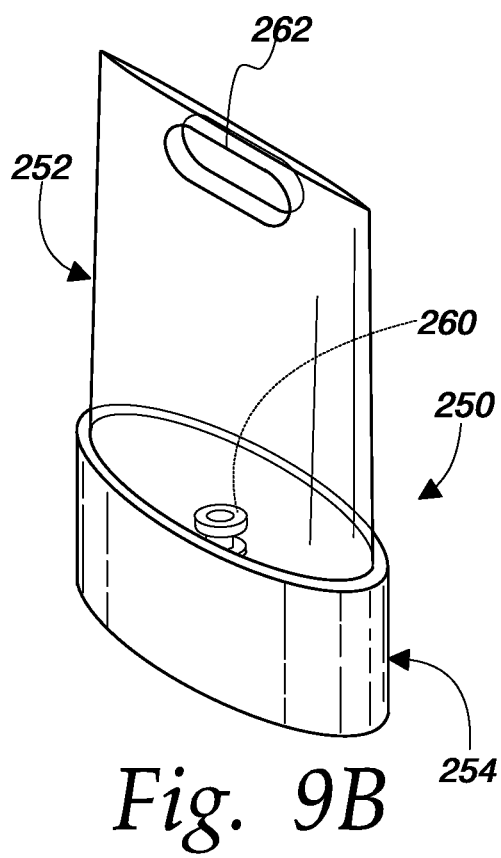
FIG. 9B is an assembled, rear perspective view of the liquid reservoir of FIG. 9.
Figure 10:
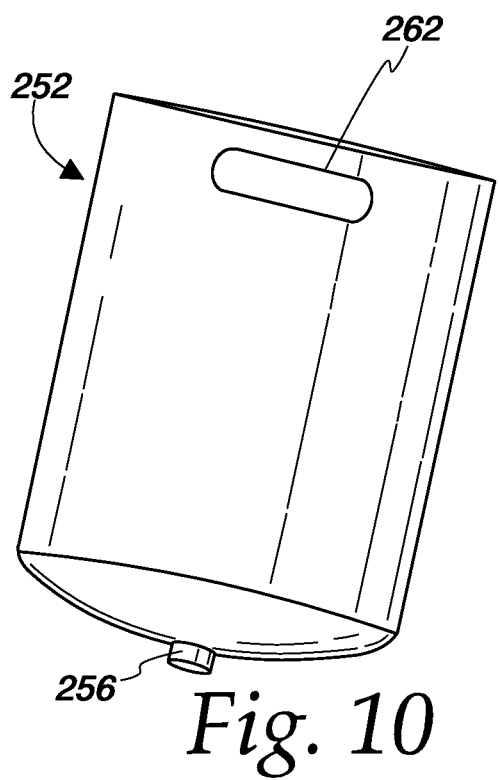
FIG. 10 is a front perspective view of a container of the liquid reservoir of FIG. 9.
Figure 10A:
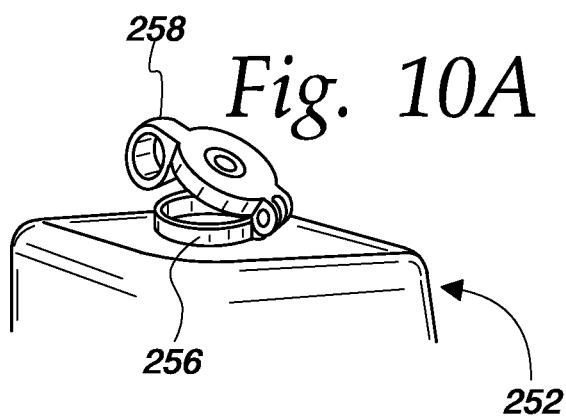
FIG. 10A is an enlarged, front perspective view of a cap of the container of FIG. 10.

Turning to FIGS. 9-11, there is shown a liquid reservoir designated as 250 and individual components thereof. The liquid reservoir 250 includes a liquid container 252 (FIGS. 10 and 10A) and a base 254 (FIG. 11). The liquid container 252 includes a pair of facing sidewalls sealed around their perimeters to define a hollow interior configured to receive an amount of an irrigant or liquid. The sidewalls of the liquid container 252 are preferably formed of a flexible material that allows the liquid container 252 to move between a collapsed or compact configuration and an expanded configuration. One end of the liquid container 252 includes a port or opening 256 extending through the sealed perimeter and included with a removable cap 258 (FIGS. 9 and 10A) that covers the port 256. The cap 258 may have a friction fit with the port 256 or the port 256 and the cap 258 may have corresponding threads so that the cap 258 may be screwed on and off the port 256 or the two may be associated together by any other suitable arrangement. The port 256 may include a valve 260 (FIGS. 9A and 9B), which may be configured as shown in FIGS. 4 and 4A and as described above. The opposite end of the liquid container 252 may include a handle 262 defined in the seal to allow an operator to grip and transport or otherwise manipulate the liquid container 252.

In between uses, the liquid container 252 may be in a collapsed configuration in which the liquid container 252 is substantially flat, with the two sidewalls next to each other and in contact. To fill the liquid container 252 with an irrigation fluid, the cap 258 is removed from the port 256 and liquid container 252 is filled through the port 256 (and the valve 260, if present). As the liquid container 252 fills, the force of the liquid on the sidewalls moves the sidewalls away from each other, expanding the liquid container 252. After the liquid container 252 is filled, the cap 258 is placed back over the port 256.

The filled liquid container 252 is then advanced cap-first into a cavity 264 defined in the top of the base 254, with the cap 258 positioned away from the port 256, as in FIGS. 9-9B. In the illustrated embodiment, the perimeter of the cavity 264 of the base 254 has a shape generally commensurate with the end of the liquid container 252 at which the cap 258 is positioned. The cavity 264 includes a conduit 266 (FIG. 11) configured to accommodate the port 256 of the liquid container 252 and place it into fluid communication with a port or opening 268 of the base 254 (FIGS. 9 and 11). The cavity 264 may include a docking formation 270 (FIG. 9) with a pin 272 that contacts and opens the valve 260 of the liquid container 252 when the port 256 of the liquid container 252 is advanced into the docking formation 270, thus allowing liquid to flow out of the liquid container 252 via the port 256 and through the conduit 266 of the base 254. The port 268 of the base 254 may be connected to a tubing segment 274 or the like (FIG. 9) to allow fluid flow to other components of the TAI system.

Figure 13:
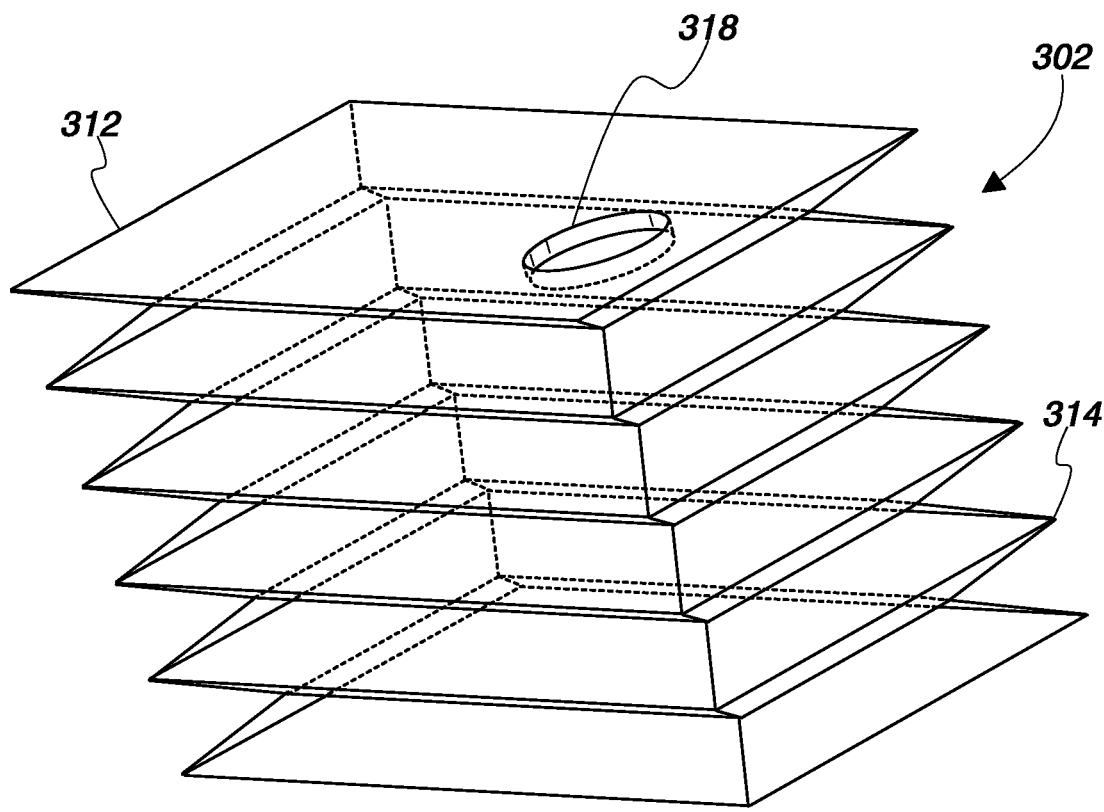
FIG. 13 is a front perspective view of a container of the liquid reservoir of FIG. 12.
Figure 14:
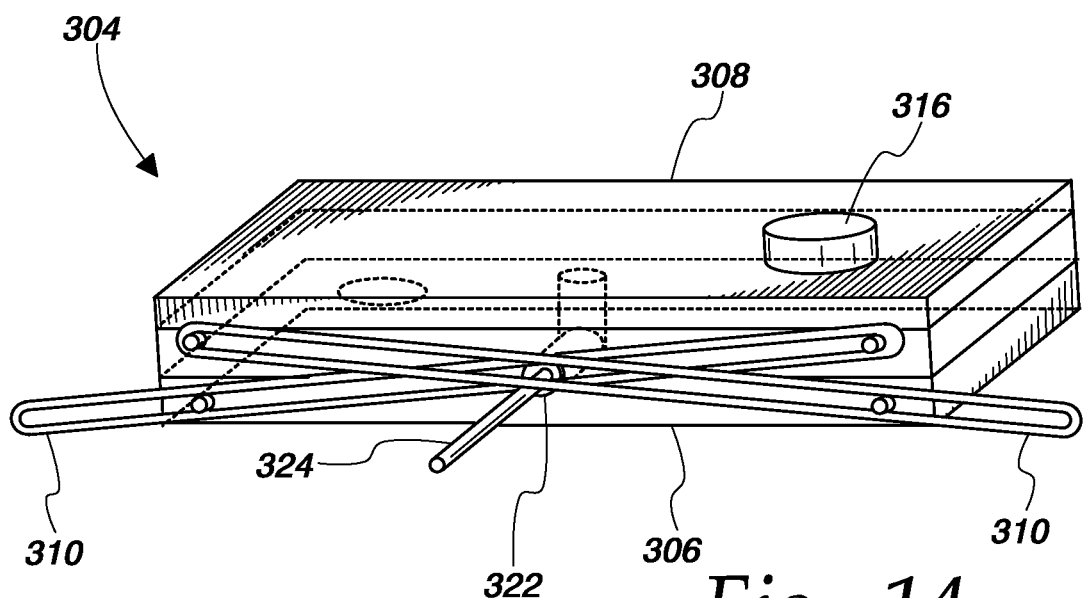
FIG. 14 is a front perspective view of a frame of the liquid reservoir of FIG. 12, with the frame shown in a collapsed condition.
Figure 15:
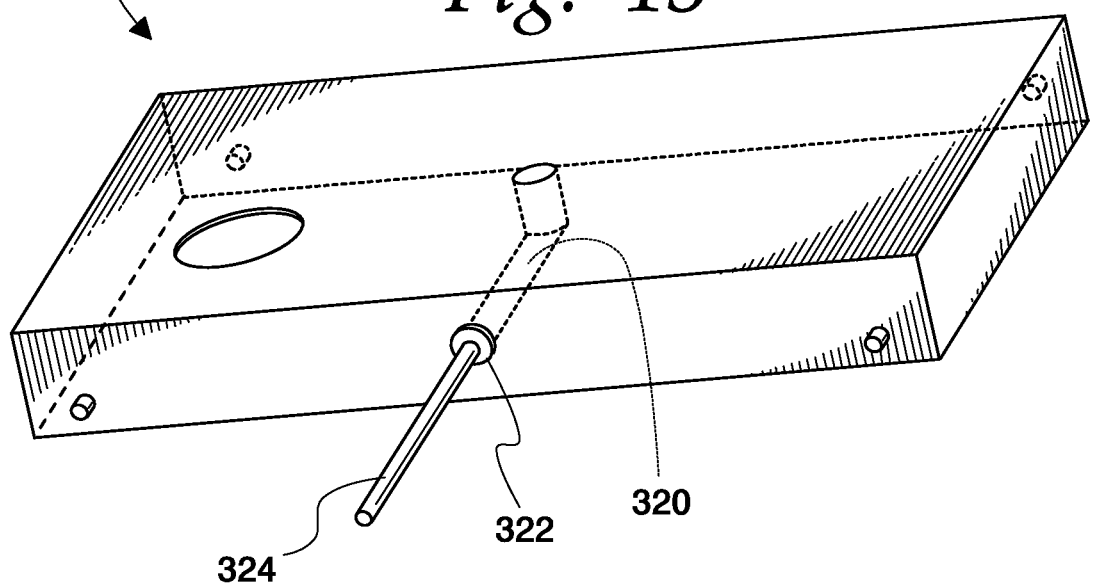
FIG. 15 is a front perspective view of a base of the frame of FIG. 14.
Figure 16:
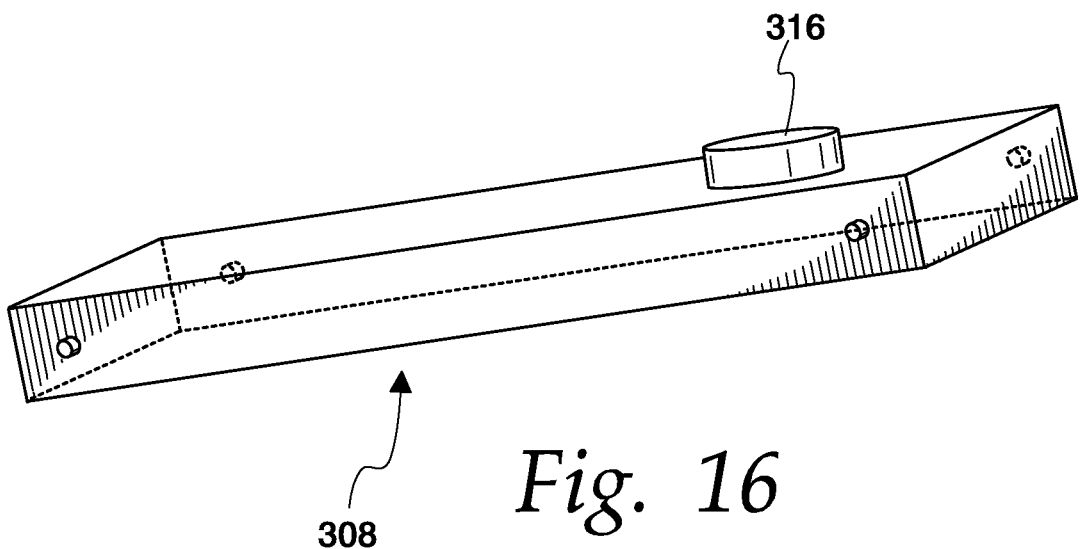
FIG. 16 is a front perspective view of a top of the frame of FIG. 14.

FIGS. 12-16 show another collapsible and expandable liquid reservoir 300 and components thereof. The liquid reservoir 300 includes a liquid container 302 (FIG. 13) and a frame 304 (FIG. 14), which includes a base 306 (FIG. 15) and a top or lid 308 (FIG. 16) connected by a pair of support struts 310 arranged in an "X" configuration on one or opposing sides of the frame 304 (FIGS. 12, 12A, and 14). The pivotal movement of the support struts 310 upon the liquid reservoir 300 being moved from an expanded condition to a collapsed condition may be understood by comparing FIGS. 12 and 12A (showing an expanded condition) to FIG. 14 (showing a collapsed condition).

The liquid container 302 may be provided generally according to the preceding description of the liquid container 102 of FIGS. 3 and 3A (i.e., with a sidewall 312 including a plurality of pleats 314, which allow the liquid container 302 to expand and collapse). FIGS. 12 and 12A show the liquid container 302 in an expanded condition, while FIG. 14 shows the liquid container 302 in a collapsed condition, in which it is fully enclosed by the frame 304. The base 306 and the top 308 may be formed of relatively rigid materials to support and protect the liquid container 302 during storage and/or transportation. In other embodiments in which the liquid container 302 does not collapse as flat as in FIG. 14, the base 306 and the top 308 of the frame 304 may be spaced apart when the liquid container 302 is in its collapsed condition. The illustrated liquid container 302 has a substantially rectangular footprint, but it should be understood that the liquid container 302 may be differently shaped without departing from the scope of the present disclosure.

In the collapsed condition, the volume defined by the sidewall 312 is relatively small (e.g., defining a volume that is smaller than the volume of liquid required during a typical TAI procedure), in which case the collapsed condition may be considered a storage or transport configuration, while the liquid container 302 may be placed into the expanded condition of FIGS. 12 and 12A for use. The top 308 may include an opening or port with a cap 316 that is removable to allow the liquid container 302 to be filled via an upper port or opening 318 (FIG. 13).

A lower port or opening of the liquid container 302 is in fluid communication (e.g, by a conduit 320 defined in the base 306) with a port 322 of the base 306, with the port 322 being configured to accommodate a tubing segment 324 or the like leading to other components of the system (e.g., a pump controller, as in FIG. 1). A valve, which may be configured as in FIGS. 4 and 4A, may be incorporated into the lower port of the liquid container 302 or into the conduit 320 or the port 322 of the base 306 for selectively allowing and preventing fluid flow therethrough.

In one exemplary method of using the liquid reservoir 300, the liquid container 302 may be moved from its expanded condition to its collapsed condition (or at least to a less expanded condition) to force irrigant in the liquid container 302 out of the port 322 of the base 306 and to a rectal catheter during a TAI procedure. In another exemplary method of using the liquid reservoir 300, the liquid container 302 may remain in an at least partially expanded condition during a TAI procedure, with a pump or the like drawing irrigant out of the liquid container 302 via the port 322 of the base 306 without moving the sidewall 312 to a more collapsed condition.

FIGS. 17-21 illustrate another embodiment of a liquid reservoir 350 and components thereof. The liquid reservoir 350 includes a liquid container 352 (FIG. 18) and a frame 354 (FIGS. 19 and 19A), which includes a base 356 (FIG. 20) and a top or lid 358 (FIG. 21) connected by a pair of support struts 360. The pivotal movement of the support struts 360 when moving the frame 354 from an expanded condition to a collapsed condition may be understood by comparing FIGS. 17 and 17A (showing an expanded condition) to FIGS. 19 and 19A (showing a collapsed condition).

Figure 17A:
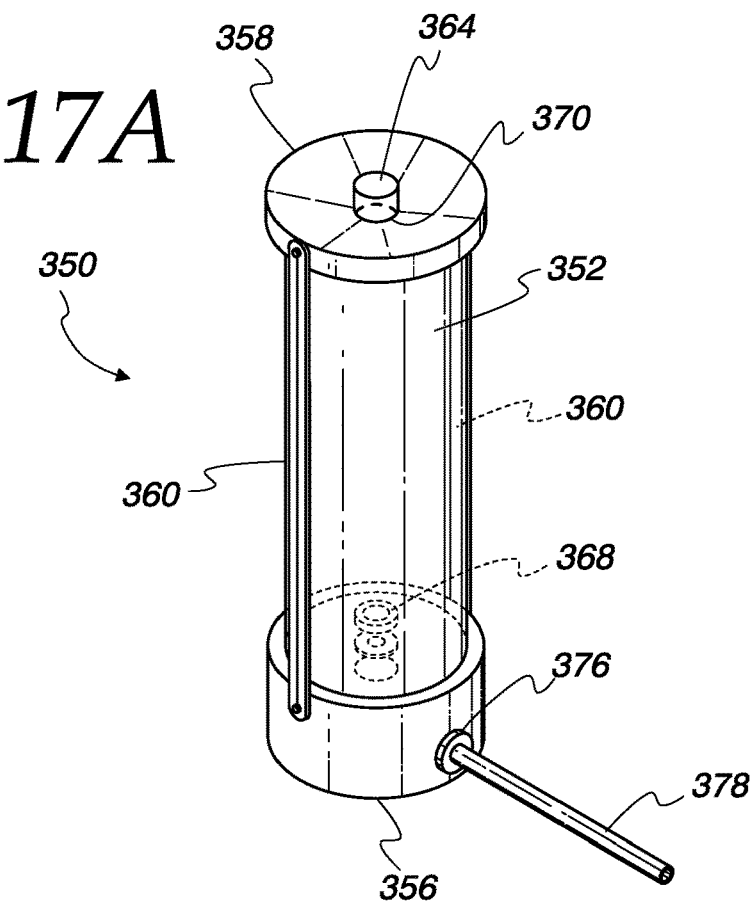
FIG. 17A is a front perspective view of the liquid reservoir of FIG. 17.
Figure 18:
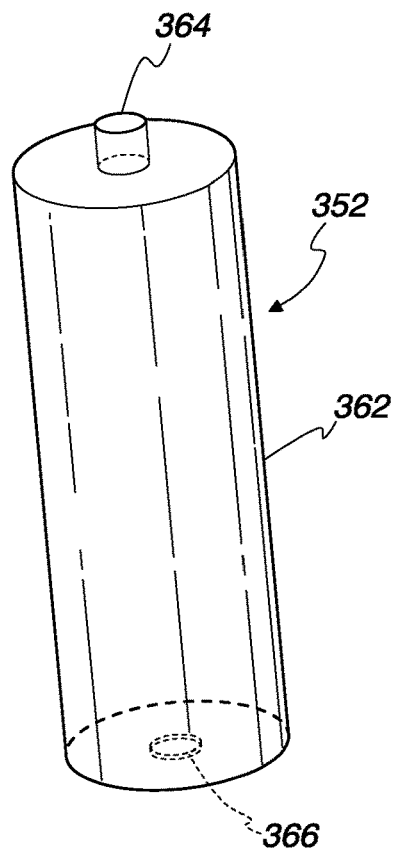
FIG. 18 is a front perspective view of a container of the liquid reservoir of FIG. 17.
Figure 21:
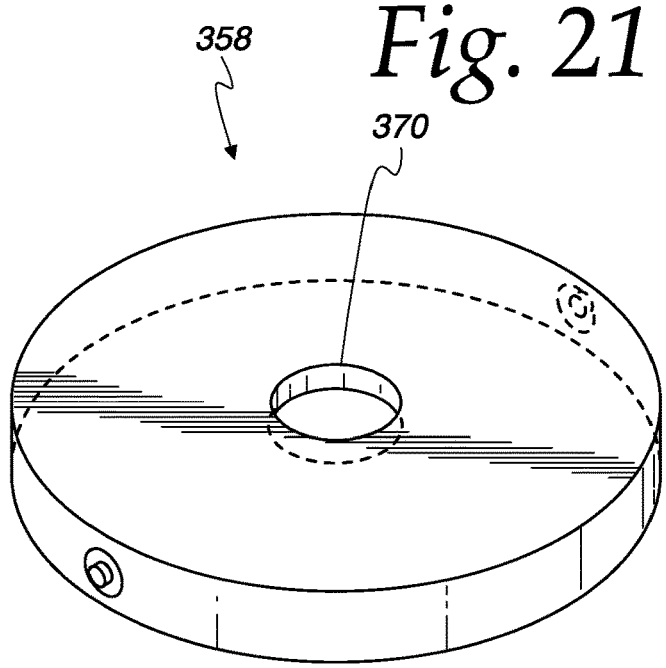
FIG. 21 is a front perspective view of a top of the frame of FIG. 19.
Figure 20:
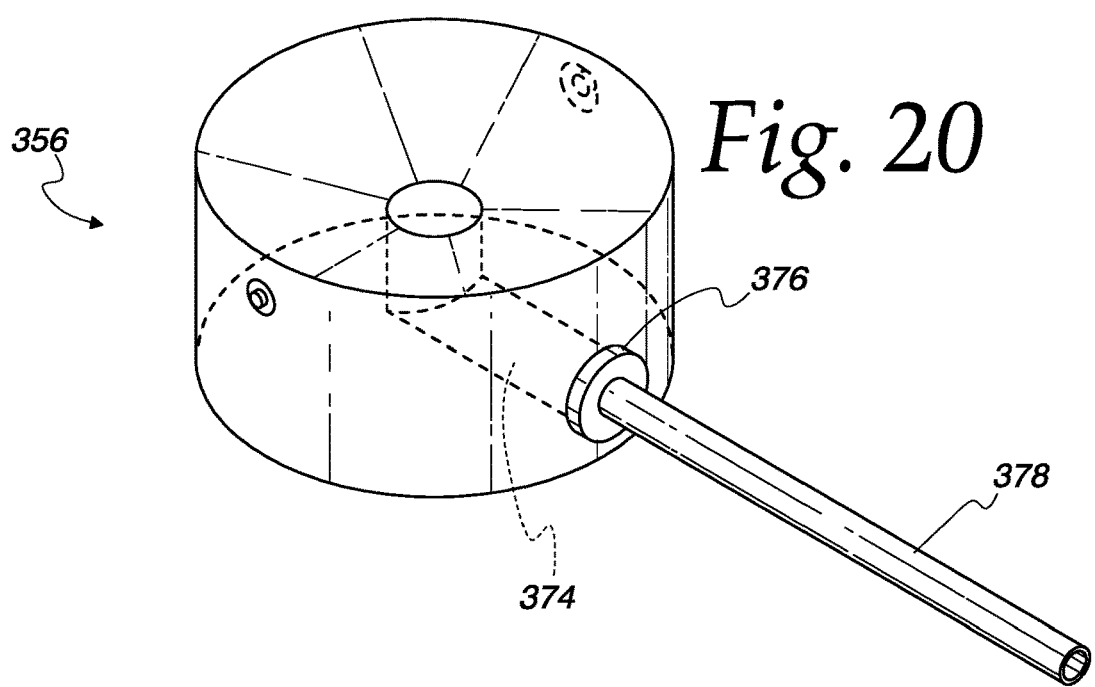
FIG. 20 is a front perspective view of a base of the frame of FIG. 19.
Figure 19:
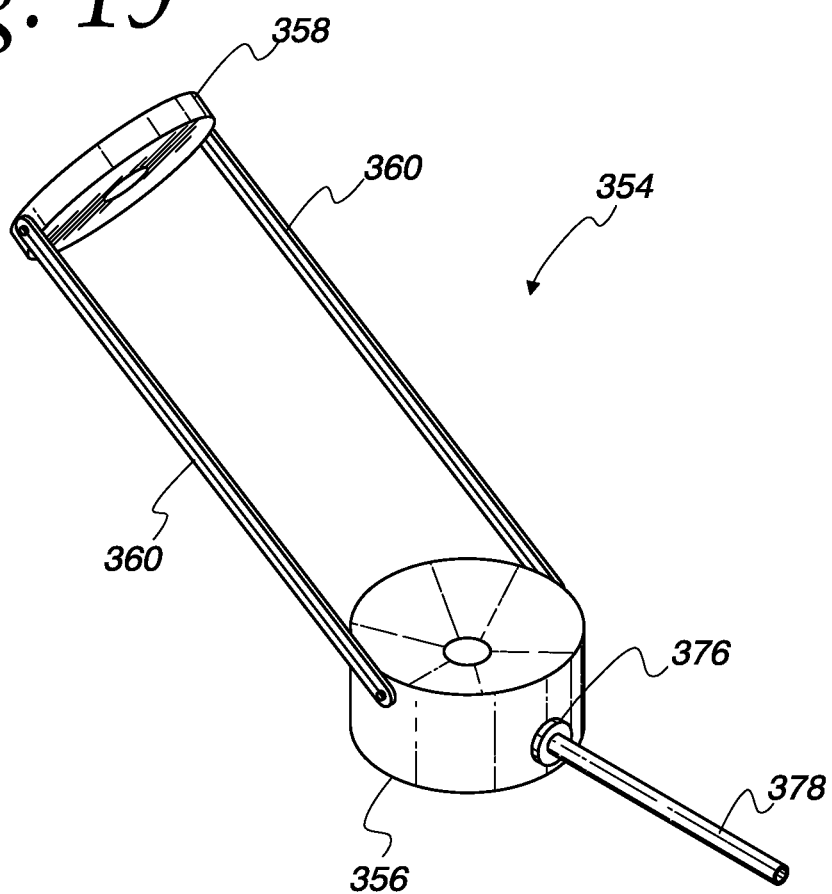
FIG. 19 is a front perspective view of a frame of the liquid reservoir of FIG. 17, with the frame shown in a partially collapsed condition.
Figure 19A:
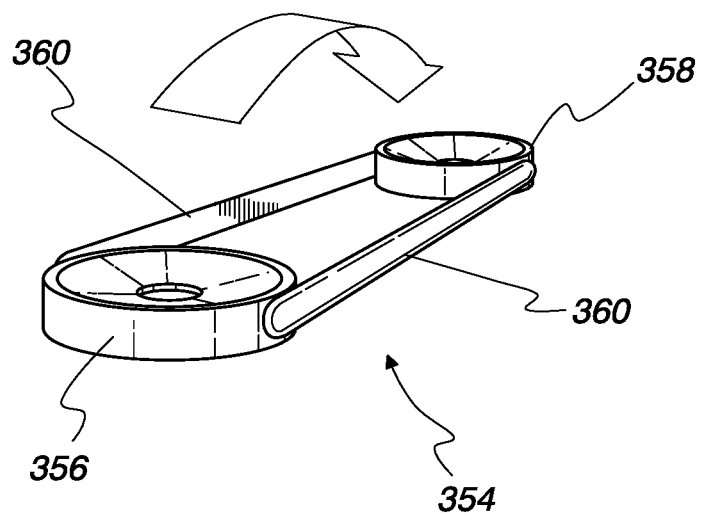
FIG. 19A is a rear perspective view of the frame of FIG. 19, with the frame shown in a collapsed condition.

The illustrated liquid container 352 is defined by a generally cylindrical or tubular sidewall 362, with a top port or opening 364 and a bottom port or opening 366 (FIG. 18). In other embodiments, the liquid container 352 may be differently shaped and/or include only a bottom port 366. The liquid container 352 is preferably formed of a generally flexible material for improved portability, but it may alternatively be formed of a generally rigid material or a semi-rigid material. The bottom port 366 may include a valve 368 (FIG. 17A), which may be configured as in FIGS. 4 and 4A. Alternatively, the valve 368 may be incorporated into the base 356.

Figure 17:
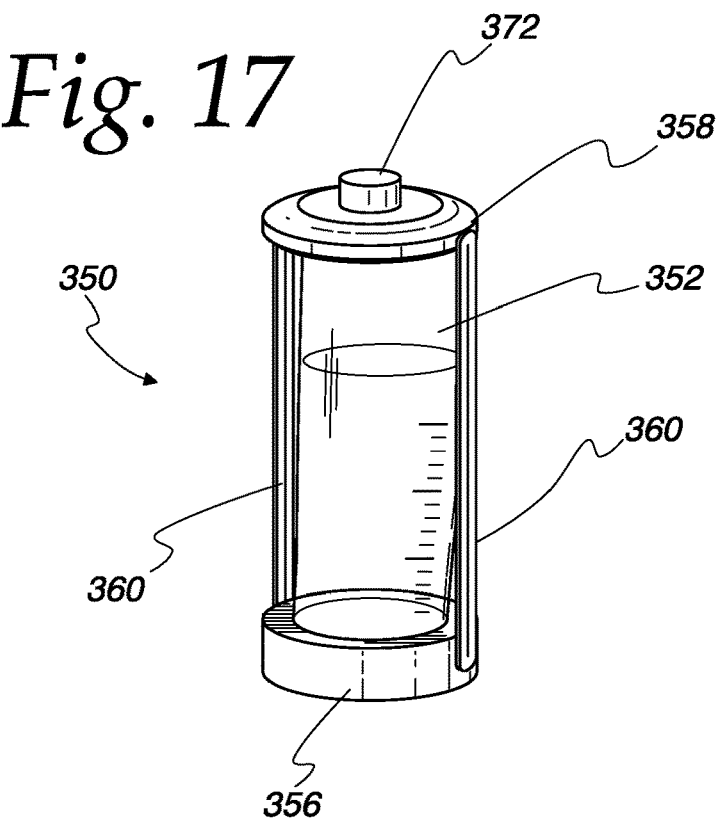
FIG. 17 is a rear perspective view of another embodiment of a liquid reservoir according to an aspect of the present disclosure.

The liquid container 352 is sized and configured to be mounted between the base 356 and the top 358 of the frame 354, as in FIGS. 17 and 17A. If the liquid container 352 includes a top port 364, it may be aligned with an upper port or opening 370 of the top 358 to allow the liquid container 352 to be filled with an irrigant through the aligned ports 364 and 370. In the illustrated embodiment, a removable cap 372 is associated with the top port 370 of the liquid container 352 (FIG. 17) and may be removed to fill the liquid container 352 with a liquid. If the liquid container 352 is formed of a flexible material, the cap 372 may bear against the top 358 of the frame 354 to prevent the liquid container 352 from collapsing within the frame 354.

The bottom end of the liquid container 352 is seated upon the base 356 of the frame 354 during a TAI procedure. A conduit 374 of the base 356 (FIG. 20) places the bottom port 366 of the liquid container 352 into fluid communication with a port or opening 376 of the base 356, which may be connected to a tubing segment 378 or the like (FIGS. 17A and 19) that is connected to another component of the TAI system (e.g., a pump controller). If the bottom port 366 of the liquid container 352 includes a valve 368, the base 356 may include a pin that contacts and opens the valve 368 when the liquid container 352 is mounted to the base 356.

Between TAI procedures, the frame 354 may be moved from its expanded condition of FIGS. 17 and 17A to a partially (FIG. 19) or fully (FIG. 19A) collapsed condition. In the illustrated embodiment, the support struts 360 are capable of at least 90° rotation to allow them to move from a substantially vertical orientation (i.e., the expanded condition of FIGS. 17 and 17A) to a substantially horizontal orientation (i.e., the flat or fully collapsed condition of FIG. 19A), which allows the frame 354 to assume a substantially flat configuration for discrete storage.

FIGS. 22-24 illustrate different embodiments of self-supporting liquid containers that do not require a frame or base to stand upright. In the embodiment of FIG. 22, a liquid container 500 includes a pair of sidewalls 502 joined around their perimeters except along their bottom edges, which instead are each sealed to a bottom surface 504. A port or opening 506 may be defined in one of the sidewalls 502 (as in the illustrated embodiment) or in the bottom surface 504 for filling the liquid container 500 with an irrigant. A lower port or opening (which may be the aforementioned port 506, if formed in the bottom surface, or a second port) may include a valve (as in FIGS. 4 and 4A) for interaction with a conduit of a frame, as described above.

The sidewalls 502 and bottom surface 504 may be formed of a generally flexible material, such that the sidewalls 502 may lay flat against each other, with the bottom surface 504 folded onto itself for flat storage and transport of the empty liquid container 500. To render the otherwise flexible liquid container 500 self-supporting, it may be provided with generally rigid edges. In one embodiment, generally rigid edges 508 are formed by applying a compressive heat seal to join the perimeters of the sidewalls 502 to each other and to the bottom surface 504, but it is within the scope of the present disclosure for generally rigid edges 508 to be formed in some other manner. The generally rigid edge 508 formed between the sidewalls 502 is configured as an arch in the illustrated embodiment, which combines with the rigid edge 508 defined around the bottom surface 504 to render the liquid container 500 self-supporting.

FIGS. 23-23B illustrate a variation of the liquid container 500 of FIG. 22. In the embodiment of FIGS. 23-23B, rather than providing a pair of joined sidewalls, a liquid container 550 is defined by a single sidewall 552 formed as a "skirt," extending between a top port or opening 554 and a bottom surface 556. As there is not a rigid arch supporting the liquid container 550, the rigid edge 558 formed between the sidewall 552 and the bottom surface 556 is relied upon for support. To that end, the bottom edge of the sidewall 552 may include two diametrically opposed slits 560, giving the bottom portion of the sidewall 552 a generally "saddle" shape. The bottom surface 556 is sealed to the bottom edge of the sidewall 552 to form a rigid sealed edge 558 along the bottom edge of the sidewall 552, with a pair of troughs 562 defined between the slits 560 (FIG. 23). The slits 560 allow the sidewall 552 to collapse upon itself for flat storage, as in FIG. 23. When the liquid container 550 is filled with an irrigant, the troughs 562 fill and flare outwardly to the configurations of FIGS. 23A and 23B to serve as feet or supports that prop up and support the filled and expanded liquid container 550, which assumes the general shape of a bell. The bottom surface 556 may include a port and associated valve for association with a base, as described above with respect to other liquid containers of the present disclosure.

FIG. 24 shows a liquid reservoir 600 having a self-supporting liquid container 602 and a base 604. The liquid container 602 is comparable to the liquid container 252 of FIG. 10, but has a bottom surface 606 with a plurality of pleats 608, as in the sidewall 108 of the liquid container 102 of FIG. 3. The pleated bottom surface 606 allows the sidewalls 610 of the liquid container 602 to collapse or lay flat for storage, with the pleats 608 collapsing onto each other. When the liquid container 602 is filled with an irrigant, the pleats 608 expand outwardly to provide a sturdy support surface for the liquid container 602. The liquid container 602, when paired with an associated base 604 (as in FIG. 24), provides a liquid source for a TAI system, in accordance with the foregoing descriptions of other liquid reservoirs of the present disclosure.

It should be understood that the features and formations of the different liquid reservoirs described herein may be combined with each other. For example, the liquid container 550 of FIGS. 23-23B may be combined with the base 104 and the top 106 of FIGS. 3 and 3A or the frame 354 of FIGS. 19 and 19A. Thus, the present disclosure is not limited to the exact configurations described and illustrated herein, but rather the aspects of the different embodiments may be interchanged and combined in various ways to provide liquid reservoirs encompassed by the present disclosure.

C. Alternative Embodiments of a Rectal Catheter

Figure 25:
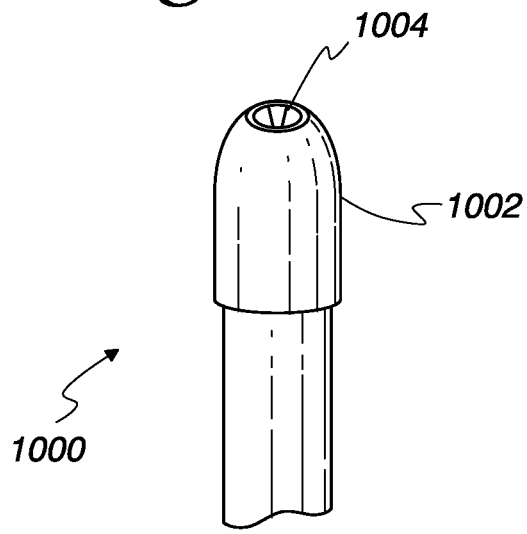
FIG. 25 is a front perspective view of a portion of a catheter according to an aspect of the present disclosure, with a retaining element of the catheter shown in a collapsed condition.
Figure 25A:
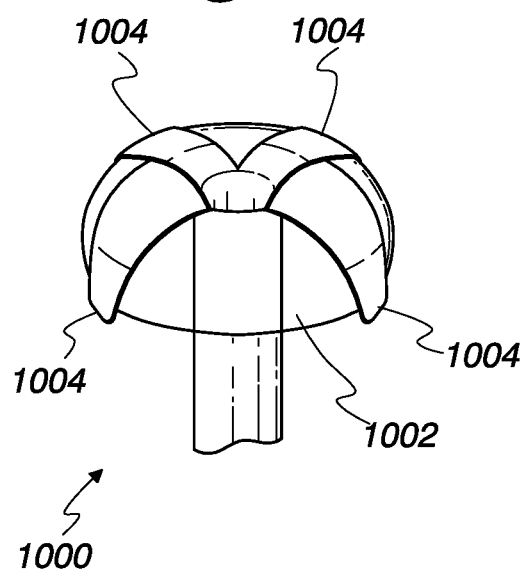
FIG. 25A is a front perspective view of the portion of the catheter of FIG. 25, with the retaining element shown in an expanded condition.
Figure 25B:
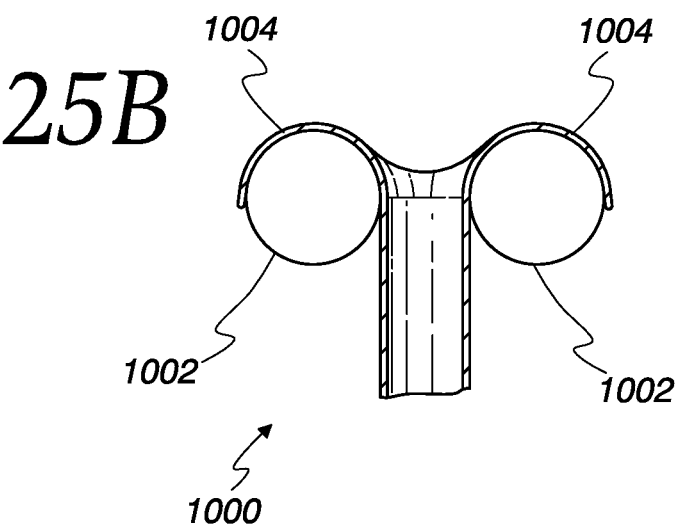
FIG. 25B is a cross-sectional view of the catheter retaining element of FIG. 25A.

FIGS. 25-25B show a retaining element 1000 that may be incorporated into a rectal catheter of the type shown in FIG. 1. In the embodiment of FIGS. 25-25B, the retaining element 1000 includes a generally toroidal balloon or expandable member 1002 that is selectively placed into fluid communication with a fluid source (e.g., a liquid reservoir of the type described herein) for receiving an expansion or inflating agent or fluid, such as air or water or an irrigant. FIG. 25 illustrates the balloon 1002 before expansion (i.e., before introduction of the expansion or inflating agent or fluid), while FIGS. 25A and 25B show the balloon 1002 following expansion. The balloon 1002 is movable between its expanded and collapsed or contracted conditions by the addition and removal of fluid to the interior of the balloon 1002.

In addition to the balloon 1002, the retaining element 1000 includes a plurality of supporting petals 1004. FIG. 25A shows four supporting petals 1004, but it should be understood that the number of supporting petals 1004 may vary without departing from the scope of the present disclosure. The supporting petals 1004 are spaced apart from each other, with FIG. 25A showing each supporting petal 1004 spaced approximately 90° from the adjacent supporting petals 1004 about a central axis of the retaining element 1000. In other embodiments, adjacent supporting petals may be separated by a different angle (e.g., three supporting petals each separated from adjacent supporting petals by 120°). While it may be advantageous for the supporting petals 1004 to be evenly spaced about the central axis of the retaining element 1000 for uniform support, it is also contemplated that adjacent supporting petals may be separated from each other by different angles (e.g., a supporting petal that is spaced 90° from one adjacent supporting petal and 120° from another adjacent supporting petal).

The illustrated embodiment shows substantially identical supporting petals 1004, with each occupying an approximately 30° arc about a central axis of the retaining element 1000 (FIG. 25A) and arcing outwardly away from the central axis to overlay approximately 180° of the circular cross-section of the balloon 1002 (FIG. 25B). While it may be advantageous for the supporting petals 1004 to be substantially identical (as in the illustrated embodiment) for uniform support, it is also within the scope of the present disclosure for at least two of the supporting petals of a retaining element to be differently configured. For example, one supporting petal may be wider (i.e., occupy a greater arc about the central axis) than another supporting petal and/or may be longer (i.e., occupy a greater arc away from the central axis) than another supporting petal.

In one embodiment, the supporting petals 1004 are configured to move from a collapsed condition to an expanded condition with the expanding balloon 1002. In the collapsed condition of FIG. 25, the supporting petals 1004 lay flat against the flat balloon 1002. The supporting petals 1004 may lay flat against an inner surface of the flat balloon 1002, the outer surface of the flat balloon 1002, or may overlay portions of both the inner and outer surfaces of the flat balloon 1002. Upon inflating or otherwise expanding the balloon 1002, the supporting petals 1004 move from their collapsed condition of FIG. 25 to their expanded, arcing condition of FIGS. 25A and 25B. This may be achieved by adhering or otherwise securing the supporting petals 1004 to the balloon 1002 to tie movement of the balloon 1002 to movement of the supporting petals 1004.

Regardless of the particular configuration of the supporting petals 1004, they serve to provide increased structural integrity to the balloon 1002, preventing the balloon 1002 from bursting due to overexpansion. Depending on the rigidity of the supporting petals 1004, they may also help to control the shape of the balloon 1002 when it is inflated, for a more desirable expanded configuration.

Figure 26:
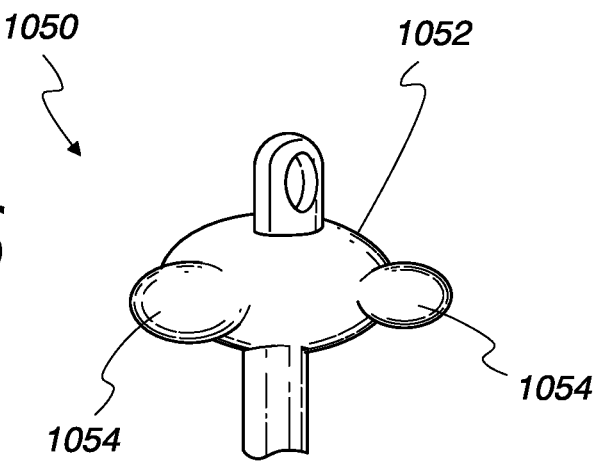
FIG. 26 is a front perspective view of a portion of another embodiment of a catheter according to an aspect of the present disclosure.

FIG. 26 illustrates another embodiment of a retaining element 1050. In the embodiment of FIG. 26, a balloon or expandable member 1052 (which is shown as being generally toroidal, but may be differently configured) is provided with a plurality of smaller balloons or expandable members 1054 (which may be referred to as "mini-balloons" or "secondary balloons") spaced about its outer perimeter. Each mini-balloon 1054 may open into the balloon 1052 (which may be referred to as a "primary balloon"), such that inflation or expansion of the primary balloon 1052 also causes inflation or expansion of the secondary balloons 1054.

FIG. 26 shows a retaining element 1050 with three secondary balloons 1054 (two of which are visible), but it should be understood that the number of secondary balloons 1054 may vary without departing from the scope of the present disclosure. The secondary balloons 1054 are spaced apart from each other, with FIG. 26 showing each secondary balloon 1054 spaced approximately 120° from the adjacent secondary balloons 1054 about a central axis of the retaining element 1050. In other embodiments, adjacent secondary balloons 1054 may be separated by a different angle (e.g., five secondary balloons each separated from adjacent secondary balloons by 72°). While it may be advantageous for the secondary balloons 1054 to be evenly spaced about the central axis of the retaining element 1050 for uniform support, it is also contemplated that adjacent secondary balloons may be separated from each other by different angles (e.g., a secondary balloon that is spaced 90° from one adjacent secondary balloon and 120° from another adjacent secondary balloon).

The illustrated embodiment has substantially identical secondary balloons 1054, with each having a diameter that is less than half the diameter of the primary balloon 1052 (e.g., approximately one third the diameter of the primary balloon 1052, in one embodiment). While it may be advantageous for the secondary balloons 1054 to be substantially identical (as in the illustrated embodiment) for uniform support, it is also within the scope of the present disclosure for at least two of the secondary balloons of a retaining element to be differently configured. For example, one secondary balloon may be larger and/or differently shaped than another secondary balloon.

Regardless of the particular configuration of the secondary balloons 1054, they serve to improve the retention properties of the retaining element 1050 within the rectum while minimizing the surface area of balloon material in contact with the rectal wall.

Figure 27:
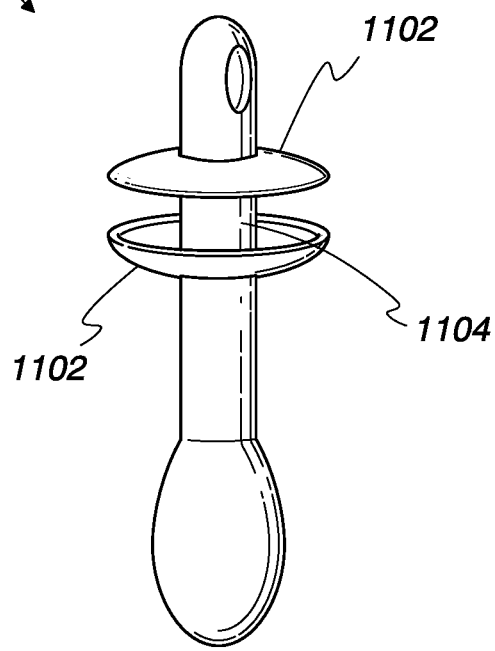
FIG. 27 is a front perspective view of a portion of another embodiment of a catheter according to an aspect of the present disclosure, with a retaining element of the catheter shown in a collapsed condition.
Figure 27A:
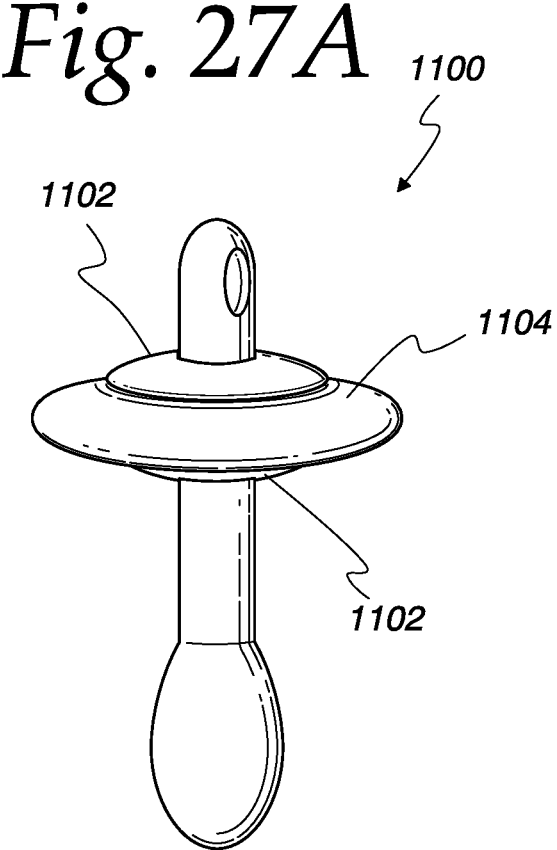
FIG. 27A is a front perspective view of the portion of the catheter of FIG. 27, with the retaining element shown in an expanded condition.

FIGS. 27 and 27A illustrate another embodiment of a retaining element 1100. In the embodiment of FIGS. 27 and 27A, the retaining element 1100 includes a pair of cuffs 1102 that are spaced along a central axis of the retaining element 1100. A balloon or expandable member 1104 is positioned between the cuffs 1102 and configured to inflate or otherwise expand to come into contact with at least one (but preferably both) of the cuffs 1102, as in FIG. 27A. The presence of the cuffs 1102 limits the ability of the balloon 1104 to expand in an axial direction (i.e., along the central axis), instead forcing the balloon 1104 to expand in the radial or outward direction. This prevents the balloon 1104 from assuming an "olive" shape, which is common among a number of conventional retaining elements and which is not ideal for retention within the rectum. Instead, the presence of the cuffs 1102 enforces a substantially toroidal configuration for the expanded balloon 1104, as in FIG. 27A.

The cuffs 1102 may be variously configured without departing from the scope of the present disclosure, but are preferably un-inflatable or otherwise have a substantially fixed shape and configuration with an outer diameter or dimension that is less than the outer diameter or dimension of the expanded balloon 1104. In the illustrated embodiment, each cuff 1102 is generally frusto-conical or cymbal-shaped, with the maximum diameters of the cuffs 1102 facing each other. The illustrated cuffs 1102 are substantially identical, which may be advantageous for symmetrical expansion of the balloon 1104, but it is also within the scope of the present disclosure for the cuffs to be differently configured.

Figure 28:
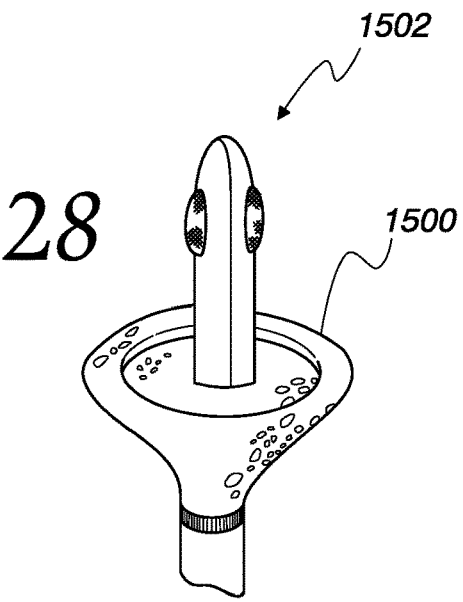
FIG. 28 is a front perspective view of a portion of another embodiment of a catheter according to an aspect of the present disclosure.
Figure 28A:
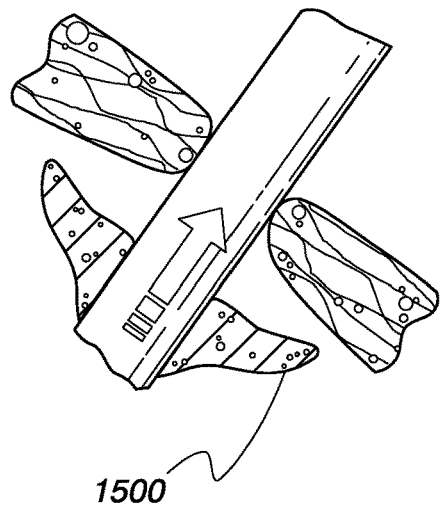
FIGS. 28A-28C illustrate a retaining element of the catheter of FIG. 28 as it is advanced into a hollow organ.
Figure 28B:
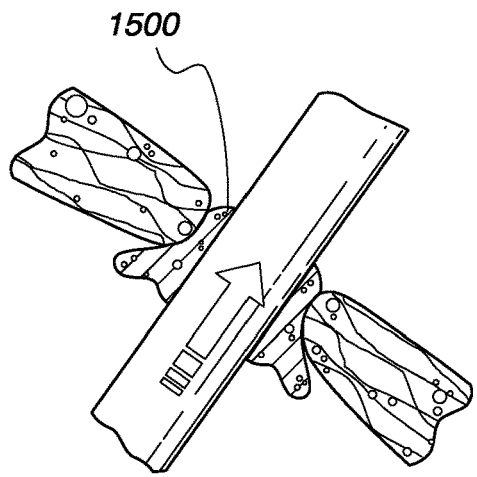
Figure 28C:
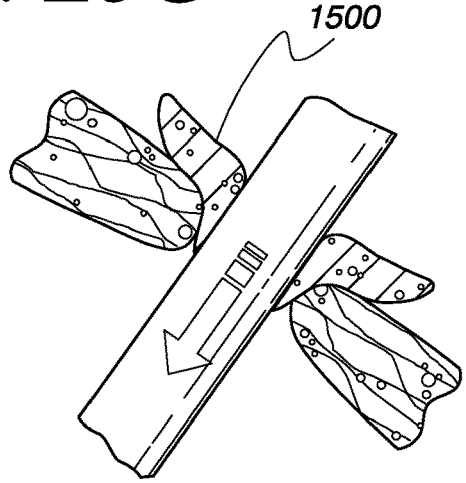

FIGS. 28-38A show un-inflatable retaining elements and/or components thereof (i.e., retaining elements that need not be provided in fluid communication with the liquid reservoir of the TAI system or with some other inflation fluid, such as air), which may decrease the cost of the rectal catheter. In the embodiment of FIG. 28, a retaining element 1500 is formed of a deformable solid material, such as a foam material. It may be advantageous for the retaining element 1500 to be formed of a closed-cell foam material to prevent liquid penetration. The retaining element 1500 may be variously configured, provided that it is capable of deforming from an initial, large diameter or dimension configuration (FIG. 28A) prior to advancement into the rectum to a collapsed, small diameter or dimension configuration (FIG. 28B) during advancement into the rectum, and then springing back to the large diameter or dimension configuration upon full insertion of the retaining element 1500 into the rectum (FIG. 28C). This automatic recovery of the large diameter or dimension configuration provides tactile feedback to signal to a user that the retaining element 1500 has been properly and fully inserted into the rectum. Following use, the rectal catheter 1502 is withdrawn from the rectum, with the shape of the retaining element 1500 changing in a sequence illustrated by FIG. 28C, FIG. 28B (during removal), and then FIG. 28A (upon removal from the rectum).

One suitable shape (which is similar to an inverted bell) is shown in FIGS. 28-28C, in which the retaining element 1500 flares outwardly from a minimum diameter to a maximum diameter in the insertion direction of the rectal catheter 1502. The retaining element 1500 may be thinner at its outer edge than at its inner surface (e.g., tapered from a minimum thickness at the outer edge to a maximum thickness at the inner surface, as in the illustrated embodiment) to increase the flexibility of the retaining element 1500 in the vicinity of its outer edge, which is the portion that must deform the most during advancement into the rectum. This flexibility also allows the retaining element 1500 to adapt to different rectal anatomies after insertion into the rectum.

Figure 29:
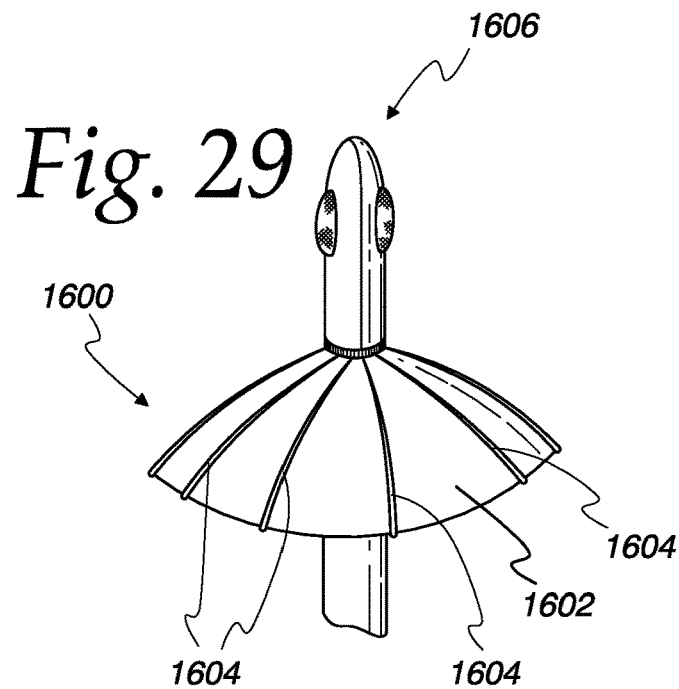
FIG. 29 is a front perspective view of a portion of another embodiment of a catheter according to an aspect of the present disclosure.
Figure 29A:
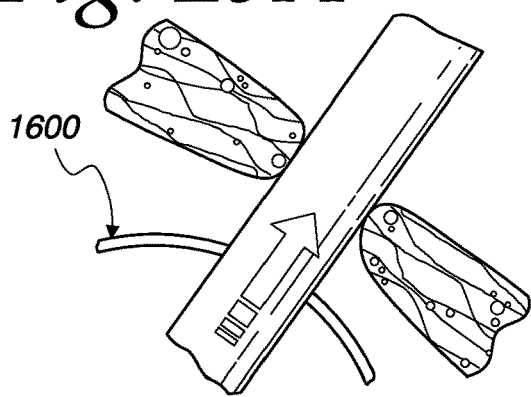
FIGS. 29A-29C illustrate a retaining element of the catheter of FIG. 29 as it is advanced into a hollow organ.
Figure 29B:
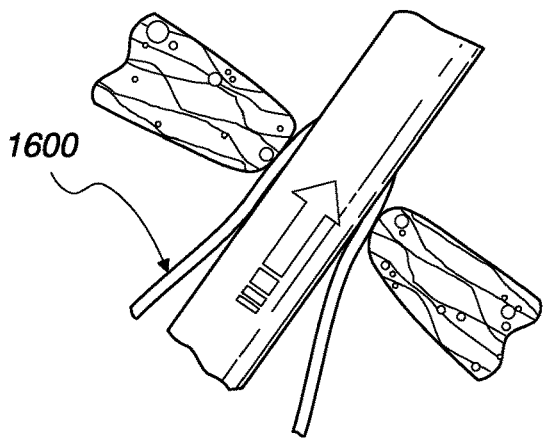
Figure 29C:
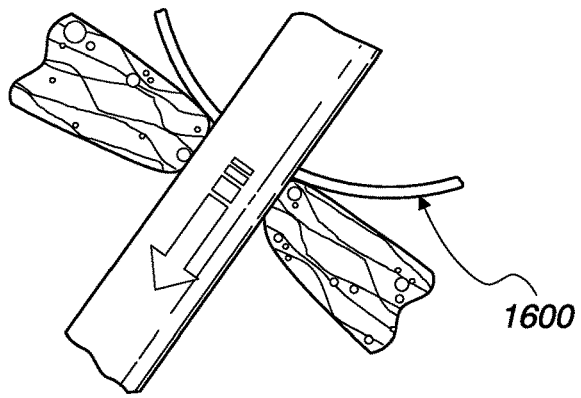

In the embodiment of FIG. 29, a retaining element 1600 has a body 1602 formed of a deformable solid material, such as silicone. The body 1602 of the retaining element 1600 may be variously configured (e.g., provided in a generally circular shape) and be supported by a plurality of soft structural ribs 1604, thus giving the retaining element 1600 the general structure and shape of an umbrella. The ribs 1604 (and, hence, the retaining element 1600) are deformable from an initial, large diameter or dimension configuration (FIG. 29A) prior to advancement into the rectum to a collapsed, small diameter or dimension configuration (FIG. 29B) during advancement into the rectum. Upon being fully advanced into the rectum, the ribs 1604 (and, hence, the retaining element 1600) resiliently deform from the collapsed, small diameter or dimension configuration of FIG. 29B to a second large diameter or dimension configuration (FIG. 29C). The two large diameter or dimension configurations may be substantially identical or may be different, as in the illustrated embodiment in which the second configuration (FIG. 29C) is an inversion of the initial configuration (FIG. 29A). The inverted configuration of FIG. 29C may be advantageous in that the retaining element 1600 acts as a cup in such a configuration to seal the rectal ledge from leakage. Upon completion of irrigation, the rectal catheter 1606 is withdrawn from the rectum, with the shape of the retaining element 1600 changing in a sequence illustrated by FIG. 29C, FIG. 29B (during removal), and then FIG. 29A (upon removal from the rectum).

FIGS. 30-30C illustrate a variation of the embodiment of FIG. 28. The retaining element 1650 of FIGS. 30-30C has the general shape of a chalice, with a cuff 1652 and a deadstop 1654 separated by a necked-down portion 1656. The cuff 1652 may be variously configured, such as being generally cup- or inverted umbrella-shaped, as in the second expanded configuration of the retaining element 1650 of FIG. 29C. As in the embodiment of FIG. 28, the cuff 1652 (regardless of its particular shape) is configured to deform from an initial large diameter or dimension configuration prior to insertion (FIG. 30A) to a collapsed, small diameter or dimension configuration during insertion (FIG. 30B), and then back to the initial configuration upon full insertion (FIG. 30C).

The deadstop 1654 is a radial extension or flange (shaped as a circle, in the illustrated embodiment) that is preferably less flexible or deformable than the cuff 1652, which may be achieved by providing the deadstop 1654 with a greater wall thickness than the associated cuff 1652. The deadstop 1654 is sufficiently inflexible to resist being advanced into the rectum, thereby preventing over-insertion of the rectal catheter 1658 into the rectum. The necked-down portion 1656 which separates the cuff 1650 and the deadstop 1654 is sized to traverse the trans-sphincteric zone, with the cuff 1650 positioned within the rectum and the deadstop 1654 positioned outside the rectum. In addition to the tactile feedback provided by the resilient deformation of the cuff 1652 within the rectum, the deadstop 1654 also provides tactile feedback to indicate to the user that the rectal catheter 1658 has been properly inserted.

Figure 31:
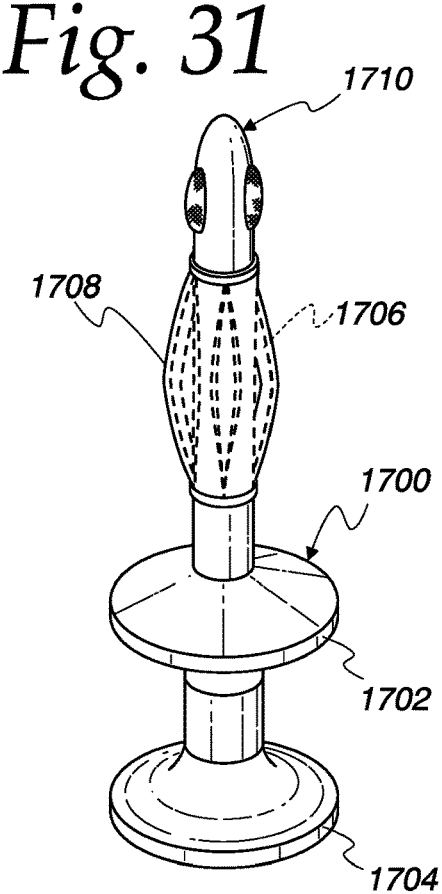
FIG. 31 is a front perspective view of a portion of another embodiment of a catheter according to an aspect of the present disclosure.
Figure 31A:
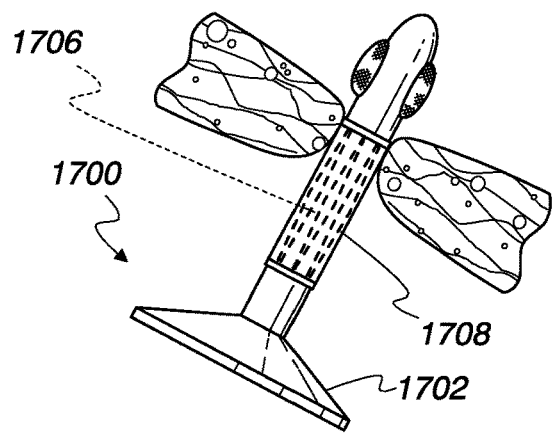
FIGS. 31A-31C illustrate a retaining element of the catheter of FIG. 31 as it is advanced into a hollow organ.
Figure 31B:
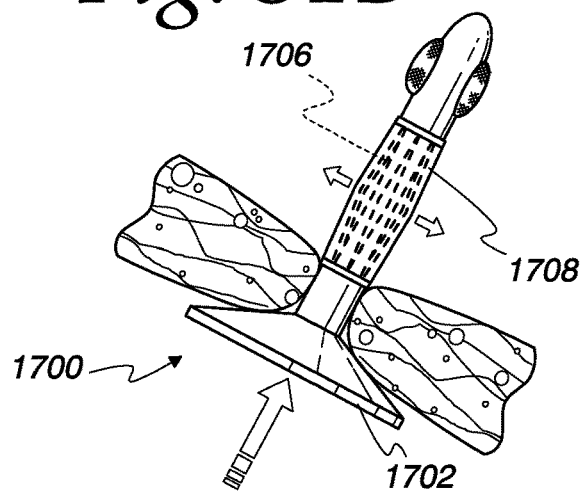
Figure 31C:
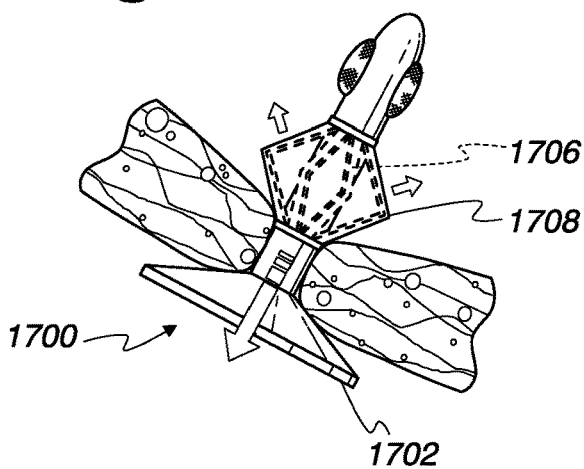

FIG. 31 shows a retaining element 1700 having a pair of deadstops 1702 and 1704, which may each be configured similarly to the deadstop 1654 of FIG. 30. In the embodiment of FIG. 31, the retaining element 1700 includes a plurality of struts 1706 (which may be enclosed within a sheath or sleeve 1708) defined by a plurality of axial slits in place of the cuff 1650 of FIG. 30. The struts 1706 are deformable from an initial collapsed configuration having a small diameter or dimension (FIG. 31A) to a partially expanded configuration with a larger diameter or dimension (FIG. 31B) to a fully expanded configuration with a maximum diameter or dimension (FIG. 31C) and back to the initial configuration.

The struts 1706 are moved to their different configuration by relative movement of the deadstops 1702 and 1704 with respect to each other. In particular, the struts 1706 are advanced into the rectum in their initial configuration until a first or upper deadstop 1702 prevents further advancement. At that time, a second or lower deadstop 1704 is moved toward the first or upper deadstop 1702 to cause the struts 1706 to deform and bow outwardly, as in FIGS. 31B and 31C. The retaining element 1700 may be provided with a locking mechanism to lock the deadstops 1702 and 1704 in place with the struts 1706 in their fully expanded configuration of FIG. 31C for irrigation. When irrigation is complete, the second or lower deadstop 1704 is moved away from the first or upper deadstop 1702 to retract the struts 1706 to their initial configuration of FIG. 31A, at which time the rectal catheter 1710 may be withdrawn from the rectum.

Figure 32:
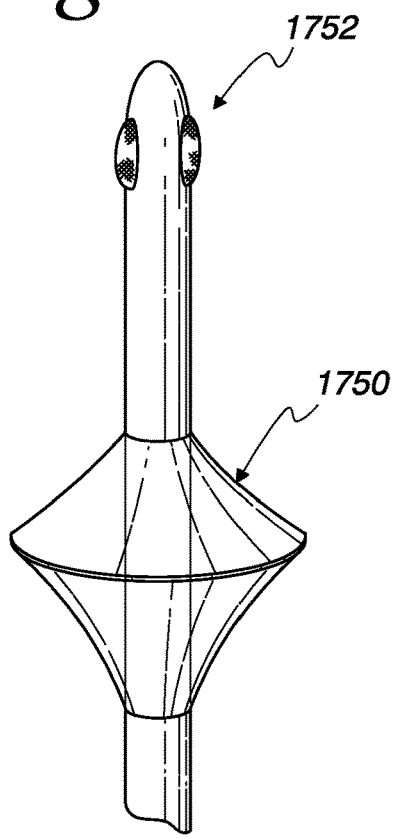
FIG. 32 is a front perspective view of a portion of another embodiment of a catheter according to an aspect of the present disclosure.
Figure 32A:
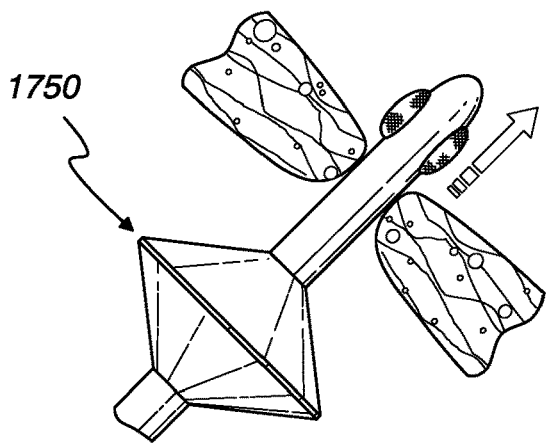
FIGS. 32A-32C illustrate a retaining element of the catheter of FIG. 32 as it is advanced into a hollow organ.
Figure 32B:
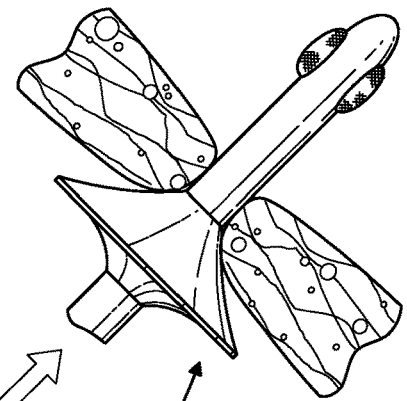
Figure 32C:
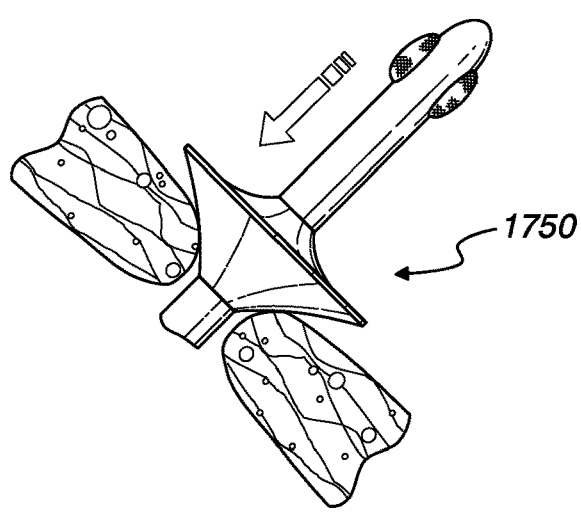

FIG. 32 illustrates a bistable retaining element 1750. In the illustrated embodiment, the retaining element 1750 is configured as a pair of circular frustums joined at their bases or maximum diameters, but it should be understood that the retaining element 1750 may be variously configured without departing from the scope of the present disclosure, provided that it is capable of moving between differently configured equilibrium states (FIGS. 32A and 32C), similar to the embodiment of FIG. 29. The retaining element 1750 is anchored at both of its ends, but is free to flex therebetween between its two equilibrium states, with the retaining element 1750 assuming its initial "joined frustum" configuration in one equilibrium state (FIGS. 32 and 32A) and a generally frusto-conical configuration in another equilibrium state (FIG. 32C).

Advancing the retaining element 1750 into the rectum causes it to move from its initial configuration (FIG. 32A) to a deformed configuration (FIG. 32B) as it enters the rectum. In the illustrated embodiment, the deformed configuration of the retaining element 1750 is a mirror image of its second equilibrium state of FIG. 32C and may itself be an equilibrium state, although it is within the scope of the present disclosure for the deformed configuration to be neither a mirror image of the second equilibrium state nor an equilibrium state itself. Upon full insertion of the retaining element 1750 into the rectum, the retaining element 1750 resiliently deforms to its second equilibrium state (FIG. 32C), which may act as a cup to seal the rectal ledge from leakage, while providing a user with tactile feedback. Upon completion of irrigation, the rectal catheter 1752 is withdrawn from the rectum, with the shape of the retaining element 1750 changing in a sequence illustrated by FIG. 32C, FIG. 32B (during removal), and then FIG. 32A (upon removal from the rectum).

Figure 33:
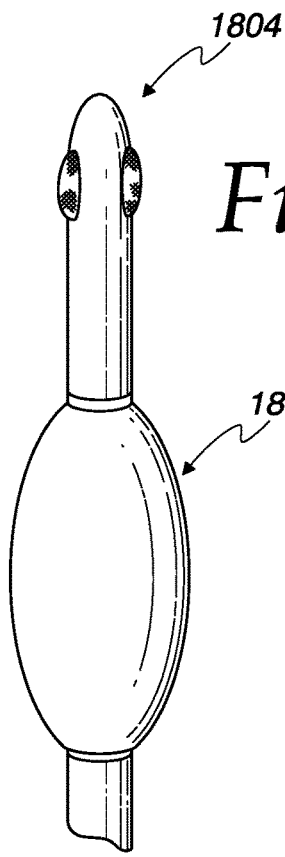
FIG. 33 is a front perspective view of a portion of another embodiment of a catheter according to an aspect of the present disclosure.
Figure 33A:
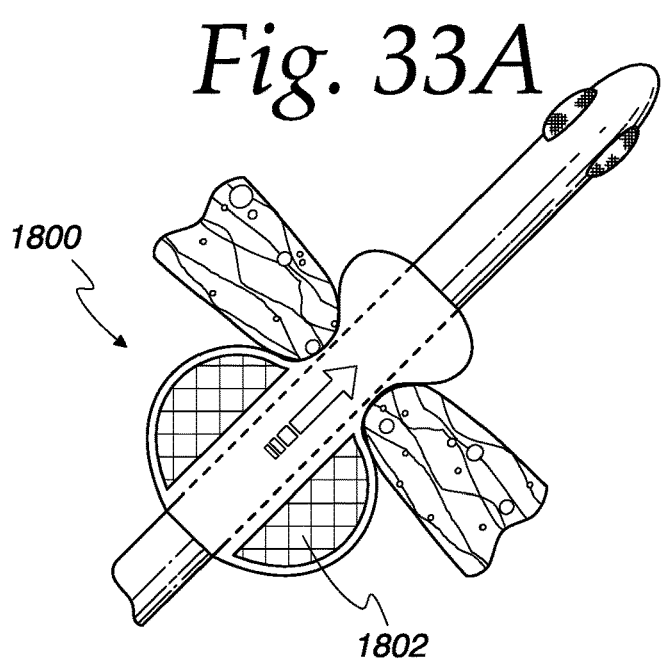
FIGS. 33A and 33B illustrate a retaining element of the catheter of FIG. 33 as it is advanced into a hollow organ.
Figure 33B:
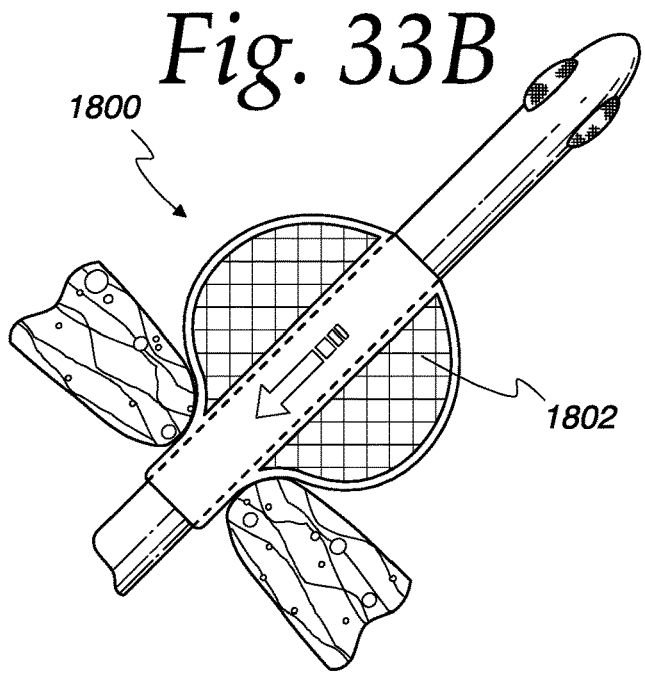

FIG. 33 shows a retaining element 1800 comprising a sealed gel balloon or pouch. The retaining element 1800 may be filled with any suitable fluid 1802, such as an oil or gel, which allows the retaining element 1800 to be compressed and deformed during insertion into the rectum (see FIGS. 33A and 33B). As the retaining element 1800 is advanced into the rectum, it is compressed inwardly toward a central axis by the sphincter (FIG. 33A), which allows the retaining element 1800 to be advanced into the rectum. Upon being fully inserted into the rectum (i.e., upon removal of the compressive force of the sphincter), the retaining element 1800 is free to expand outwardly to conform to the rectal anatomy and seal the rectal ledge from leakage. Upon completion of irrigation, the rectal catheter 1804 is withdrawn from the rectum, with the sphincter again compressing the retaining element 1800 as the retaining element 1800 is removed from the rectum.

Figure 34:
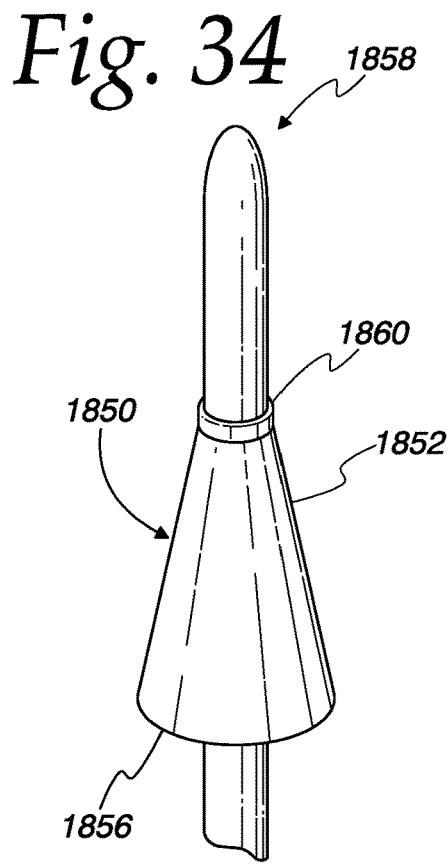
FIG. 34 is a front perspective view of a portion of another embodiment of a catheter according to an aspect of the present disclosure.
Figure 34A:
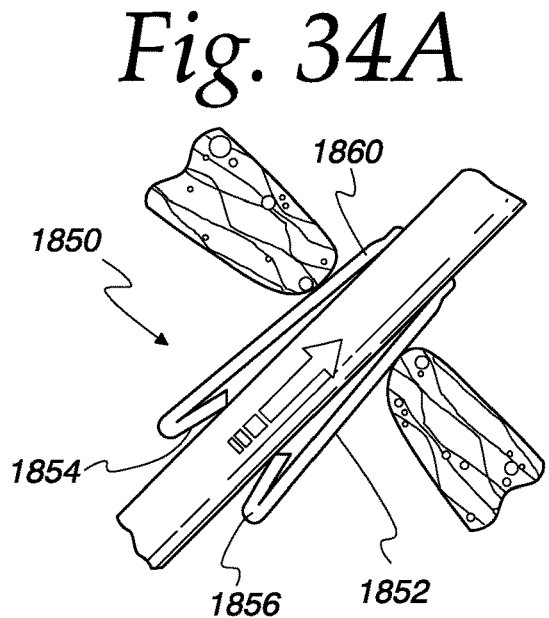
FIGS. 34A-34C illustrate a retaining element of the catheter of FIG. 34 as it is advanced into a hollow organ.
Figure 34B:
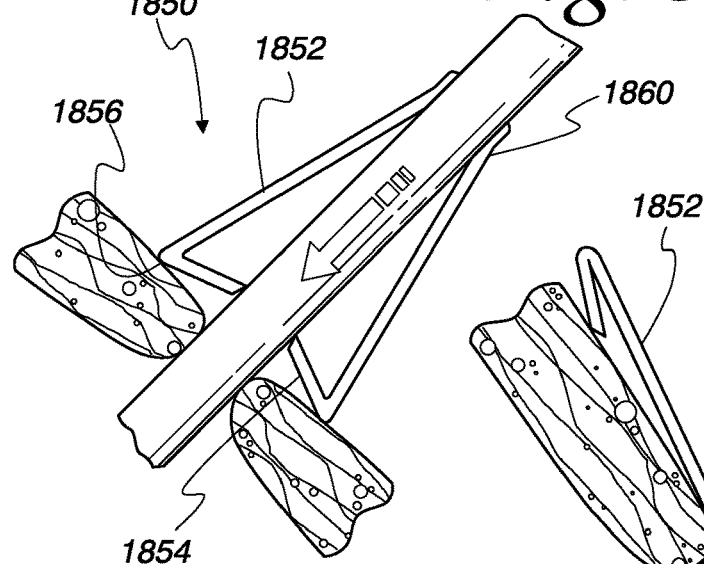
Figure 34C:
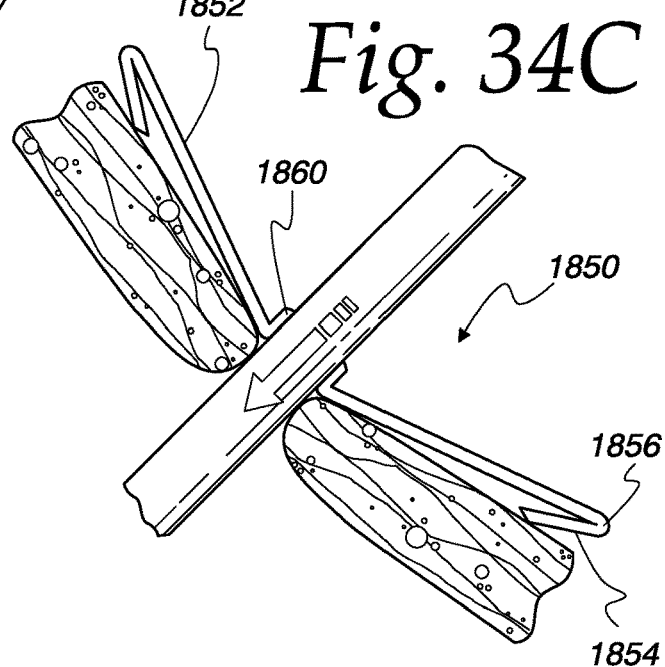

In the embodiment of FIG. 34, a retaining element 1850 is provided in a "skirt" configuration, with a downwardly extending (in the orientation of FIG. 34) body portion 1852 and an inwardly and upwardly extending flange portion 1854 (FIGS. 34A-34C) at a lower end or "hem" 1856 of the body portion 1852. The body portion 1852 is secured to the rectal catheter 1858 at an upper end 1860 and free to pivot about its upper end 1860, while the flange portion 1854 is free to move with respect to the rectal catheter 1858. The flange portion 1854 is sufficiently flexible that it may be collapsed to a relatively flat condition (compare the uncompressed condition of FIG. 34B to the compressed condition of FIG. 34A) to facilitate advancement of the retaining element 1850 into the rectum. Upon removal of the compressive force applied by the sphincter (i.e., upon full receipt of the retaining element 1850 within the rectum), the flange portion 1854 is free to deform outwardly to a larger diameter or dimension (FIG. 34B). The body portion 1852 pivots about its upper end 1860 to assume a dish shape (FIG. 34C) having a relatively large dimension or diameter within the rectum to seal the rectal ledge from leakage. Upon completion of irrigation, the rectal catheter 1858 is withdrawn from the rectum, with the retaining element 1850 deforming to a smaller diameter or dimension condition to be passed through the sphincter.

Figure 35:
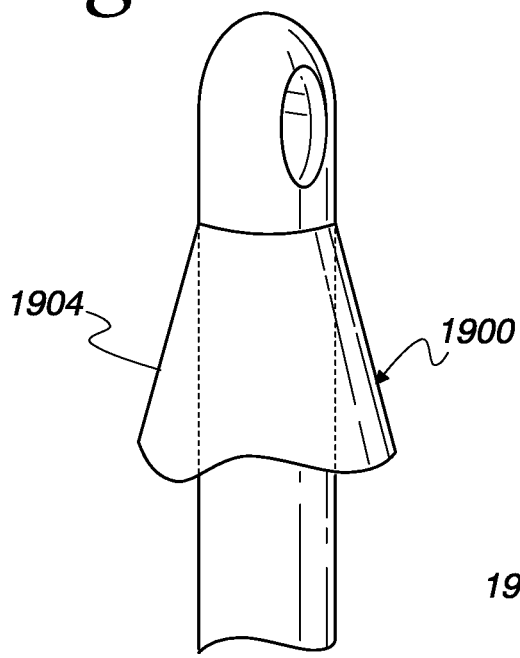
FIG. 35 is a front perspective view of a portion of another embodiment of a catheter according to an aspect of the present disclosure, with a retaining element of the catheter shown in a collapsed condition.
Figure 35A:
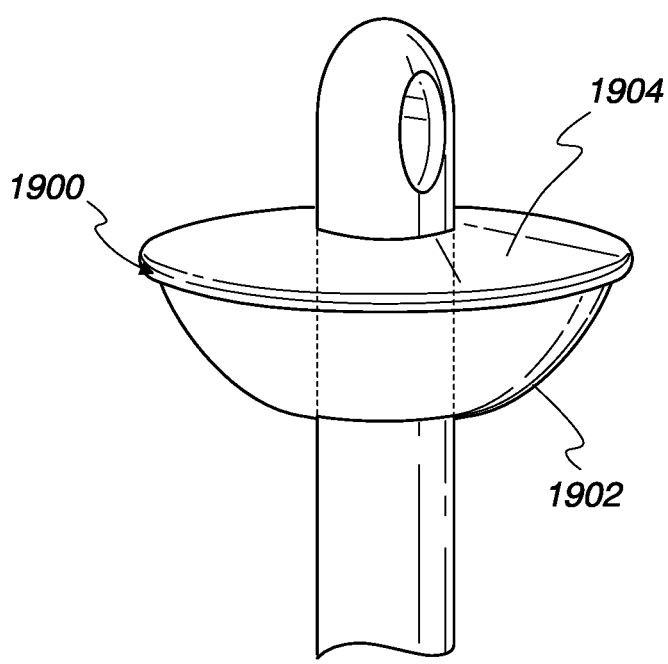
FIG. 35A is a front perspective view of the portion of the catheter of FIG. 35, with the retaining element shown in an expanded condition.
Figure 35B:
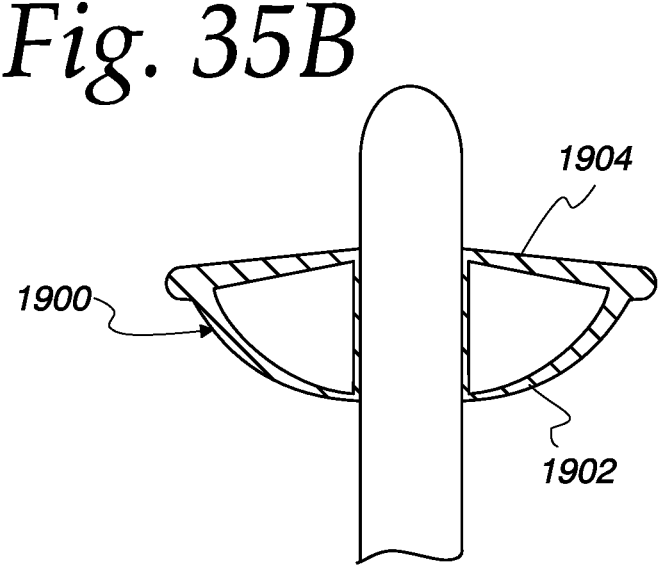
FIG. 35B is a cross-sectional view of the catheter retaining element of FIG. 35A.

FIGS. 35-35B show a retaining element 1900 with a generally hemispherical shape (FIGS. 35A and 35B) that may be moved to a deformed condition (FIG. 35) having a smaller dimension or diameter. As shown in FIGS. 35A and 35B, the retaining element 1900 may have a cup portion 1902 with a generally hemispherical shape that is closed or covered by an annular, generally radial lid portion 1904 to define a hollow interior of the retaining element 1900. The retaining element 1900 is formed of a deformable, resilient material, which allows it to be moved to a collapsed condition (FIG. 35) having a relatively small diameter or dimension to allow the retaining element 1900 to pass beyond the sphincter during advancement into and removal from the rectum. Upon full receipt of the retaining element 1900 within the rectum, it resiliently returns to its undeformed or expanded condition of FIGS. 35A and 35B to seal the rectum during irrigation, while providing a user with tactile feedback.

Figure 36:
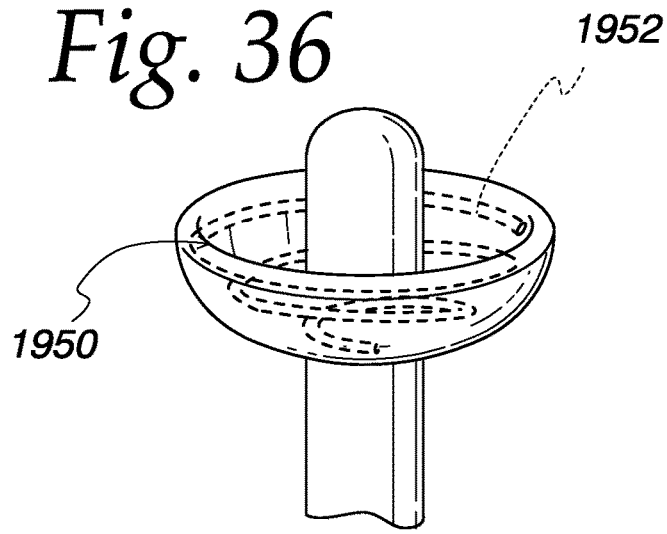
FIG. 36 is a front perspective view of a portion of another embodiment of a catheter according to an aspect of the present disclosure.
Figure 37:
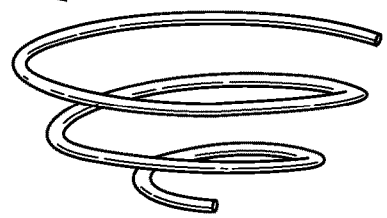
FIG. 37 is a front perspective view of a support member of a retaining element of the catheter of FIG. 36.

FIG. 36 illustrates a variation of the retaining element 1900 of FIGS. 35-35B. In the embodiment of FIG. 36, a retaining element 1950 with a generally hemispherical wall is provided with a reinforced coil member 1952 arranged as a conic spiral (as in FIG. 37) embedded therein. Alternatively, the reinforced coil member 1952 may be sealed within a hollow interior defined by the retaining element 1950. The retaining element 1950 may be provided with or without a lid portion of the type shown in FIGS. 35-35B. The retaining element 1950 of FIG. 36 functions in accordance with the foregoing description of the retaining element 1900 of FIGS. 35-35B, with the reinforced coil member 1952 ensuring that the retaining element 1952 will be compressed against the rectal ledge with more pressure than if there were no reinforced coil member. Thus, the embodiment of FIG. 36 may be preferred to the embodiment of FIGS. 35-35B if it is determined that such additional pressure is required, whereas the embodiment of FIGS. 35-35B may be preferred if lesser pressure is sufficient.

Figure 38:
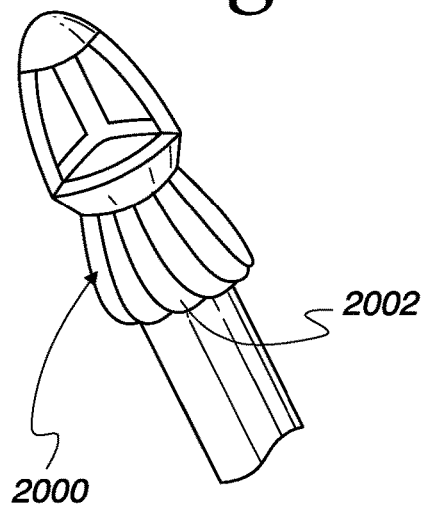
FIG. 38 is a front perspective view of a portion of another embodiment of a catheter according to an aspect of the present disclosure, with a retaining element of the catheter shown in an expanded condition.
Figure 38A:
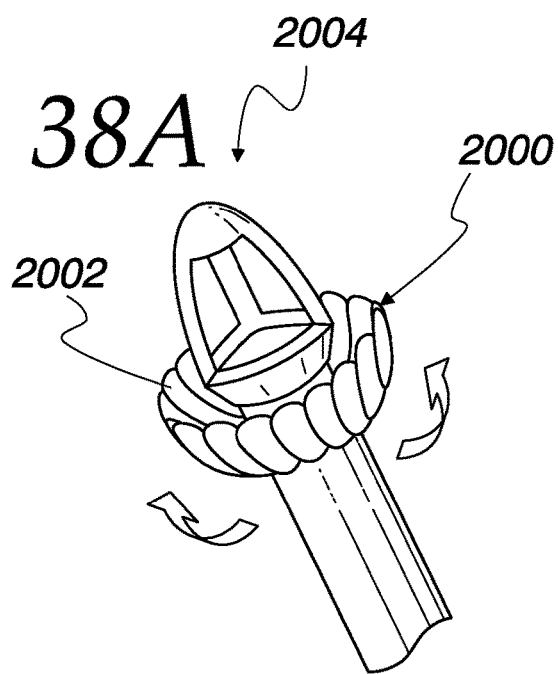
FIG. 38A is a front perspective view of the portion of the catheter of FIG. 38, with the retaining element shown in an expanded condition.

FIGS. 38 and 38A illustrate a retaining element 2000 comprising a plurality of deformable petals 2002 (which may be identically or differently configured) arranged in a ring around an outer surface of a rectal catheter 2004. In an expanded or uncompressed condition (FIG. 38A), the petals 2002 are each oriented in an upwardly arcuate configuration, combining to define a dish or cup shape. During advancement of the retaining element 2000 into the rectum, the petals 2002 are folded downwardly to lay flat against the rectal catheter 2004 (FIG. 38), in a compressed configuration having a relatively small diameter or dimension. Upon receipt of the retaining element 2000 within the rectum, the petals 2002 resiliently return to their expanded condition (FIG. 38A) to seal the rectum during irrigation, while providing a user with tactile feedback. Thereafter, the retaining element 2000 is withdrawn from the rectum, with the petals 2002 deforming to lay flat against the rectal catheter 2004 as the retaining element 2000 passes beyond the sphincter. Compared to a retaining element with a unitary or monolithic or one-piece construction, a retaining element 2000 comprising a plurality of independently deformable petals 2002 has more degrees of freedom, which may be advantageous during a TAI procedure.

It will be understood that the embodiments described above are illustrative of some of the applications of the principles of the present subject matter, with the TAI context being merely exemplary of the variety of hollow organ irrigation systems, devices, and components into which aspects of the present disclosure may be incorporated. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A liquid reservoir for a hollow organ irrigation system, comprising:
 a collapsible liquid container including a pair of facing sidewalls, each sidewall having a perimeter and the sidewalls being sealed to each other about their perimeters, each sidewall being formed of a flexible sheet of material configured to allow the sidewalls to move between a collapsed configuration and an expanded configuration, the collapsible liquid container configured to contain an irrigation liquid; and
 a base associated with an end of the collapsible liquid container, wherein
  said end of the collapsible liquid container includes a port extending away from an interior of the collapsible liquid container and a valve incorporated into the port, with the valve including a valve seat positioned within the interior of the collapsible liquid container, a valve head positioned within the interior of the collapsible liquid container and movable with respect to the valve seat, and a coil spring associated with the valve head, and the valve being configured to move between an open condition in which the valve head is spaced from the valve seat and fluid flow through the valve is allowed and a closed condition in which the valve head contacts the valve seat and fluid flow through the valve is prevented, with the coil spring biasing the valve to the closed condition,
  the base defines a docking formation configured to receive at least a portion of the port when said end of the collapsible liquid container is associated to the base,
  the docking formation includes a pin configured to contact and move the valve from the closed condition to the open condition upon said end of the collapsible liquid container being associated to the base, and
  the valve is configured to automatically move from the open condition to the closed condition upon said end of the collapsible liquid container being dissociated from the base.

2. The liquid reservoir of claim 1, wherein said end of the collapsible liquid container is positioned below an opposing end of the collapsible liquid container when said end of the collapsible liquid container is associated to the base.

3. The liquid reservoir of claim 2, further comprising a handle positioned adjacent to said opposing end.

4. The liquid reservoir of claim 1, wherein a perimeter of the base has a shape generally commensurate with said end of the collapsible liquid container.

5. The liquid reservoir of claim 1, wherein the base includes a second port and a conduit configured to direct fluid flow between the port and the second port.

6. The liquid reservoir of claim 1, wherein when the collapsible liquid container is in the collapsed configuration the liquid container is substantially flat.

7. The liquid reservoir of claim 1, wherein when the collapsible liquid container is in the collapsed configuration the sidewalls are in contact with each other.

8. The liquid reservoir of claim 1, further comprising a removable cap associated with the port.

9. The liquid reservoir of claim 1, wherein the perimeter of each sidewall contacts and is directly secured to the perimeter of the other sidewall.

10. The liquid reservoir of claim 1, wherein the docking formation is upwardly extending, generally tubular, and spaced inwardly from a perimeter of the base, with the pin being spaced inwardly of an inner surface of the docking formation.

11. A liquid reservoir for a hollow organ irrigation system, comprising:
- a collapsible liquid container including a pair of facing sidewalls, each sidewall having a perimeter and the sidewalls being sealed to each other about their perimeters, each sidewall being formed of a flexible sheet of material configured to allow the sidewalls to move between an empty collapsed configuration in which the sidewalls are in contact with each other and an expanded configuration, the collapsible liquid container configured to contain an irrigation liquid; and
- a base associated with an end of the collapsible liquid container, wherein
  - said end of the collapsible liquid container includes a port extending away from an interior of the collapsible liquid container and a valve incorporated into the port, with the valve including a valve seat positioned within the interior of the collapsible liquid container, a valve head positioned within the interior of the collapsible liquid container and movable with respect to the valve seat, and a coil spring associated with the valve head, and the valve being configured to move between an open condition in which the valve head is spaced from the valve seat and fluid flow through the valve is allowed and a closed condition in which the valve head contacts the valve seat and fluid flow through the valve is prevented, with the coil spring biasing the valve to the closed condition,
  - the base defines a docking formation configured to receive at least a portion of the port when said end of the collapsible liquid container is associated to the base,
  - the docking formation includes a pin configured to contact and move the valve from the closed condition to the open condition upon said end of the collapsible liquid container being associated to the base, and
  - the valve is configured to automatically move from the open condition to the closed condition upon said end of the collapsible liquid container being dissociated from the base.

12. The liquid reservoir of claim 11, wherein said end of the collapsible liquid container is positioned below an opposing end of the collapsible liquid container when said end of the collapsible liquid container is associated to the base.

13. The liquid reservoir of claim 12, further comprising a handle positioned adjacent to said opposing end.

14. The liquid reservoir of claim 11, wherein a perimeter of the base has a shape generally commensurate with said end of the collapsible liquid container.

15. The liquid reservoir of claim 11, wherein the base includes a second port and a conduit configured to direct fluid flow between the port and the second port.

16. The liquid reservoir of claim 11, further comprising a removable cap associated with the port.

17. The liquid reservoir of claim 11, wherein the perimeter of each sidewall contacts and is directly secured to the perimeter of the other sidewall.

18. The liquid reservoir of claim 11, wherein the docking formation is upwardly extending, generally tubular, and spaced inwardly from a perimeter of the base, with the pin being spaced inwardly of an inner surface of the docking formation.

* * * * *